US007459296B2

(12) United States Patent
Weber et al.

(10) Patent No.: US 7,459,296 B2
(45) Date of Patent: Dec. 2, 2008

(54) HEPATITIS C VIRUS NS3 HELICASE SUBDOMAIN I

(75) Inventors: Patricia C. Weber, Yardley, PA (US); Paul Reichert, Montville, NJ (US); Vincent S. Madison, Mountain Lakes, NJ (US); Daniel F. Wyss, Convent Station, NJ (US); Nanhua Yao, Irvine, CA (US); Dingjiang Liu, Edison, NJ (US); Jennifer J. Gesell, Hamilton Square, NJ (US)

(73) Assignee: Schering Corporation, Kenilworth, NJ (US)

( * ) Notice: Subject to any disclaimer, the term of this patent is extended or adjusted under 35 U.S.C. 154(b) by 1450 days.

(21) Appl. No.: 09/825,423

(22) Filed: Apr. 3, 2001

(65) Prior Publication Data

US 2004/0253577 A1 Dec. 16, 2004

Related U.S. Application Data

(60) Provisional application No. 60/194,419, filed on Apr. 4, 2000.

(51) Int. Cl.
*C12N 9/12* (2006.01)
*C07K 14/00* (2006.01)
*G01N 31/00* (2006.01)

(52) U.S. Cl. ............................ 435/194; 530/350; 436/4
(58) Field of Classification Search ................... 435/195
See application file for complete search history.

(56) References Cited

U.S. PATENT DOCUMENTS

| 5,989,827 | A | 11/1999 | Fesik et al. | |
| 6,183,121 | B1 * | 2/2001 | Kim et al. | ...................... 702/19 |
| 2004/0253577 | A1 * | 12/2004 | Weber et al. | ...................... 435/5 |

OTHER PUBLICATIONS

Benz et al., Crystal structure of the ATPase domain of translation initiation factor 4A from *Saccharomyces cerevisiae*—the prototype of the DEAD box protein family, Jun. 1, 1999, Structure, vol. 7, pp. 671-679.*
Kim et al., Hepatitis C virus NS3 RNA helicase domain with a bound oligonucleotide: the crystal structure provides insights into the mode of unwinding, 1997, Structure, vol. 6, pp. 89-100.*
Alvares et al., "Rat urate oxidase produced by recombinant baculovirus expression: formation of peroxisome crystalloid core-like structures", Jun. 1992, Proceedings of the National Academy of Sciences U S A, vol. 89, pp. 4908-4912.*
Giege et al., "Crystallogenesis of Biological Macromolecules: Facts and Perspectives", Jul. 1994; Acta Crystallographica Section D, vol. 50, pp. 339-350.*
McPherson et al., "The science of macromolecular crystallization", Aug. 1995, Structure, vol. 3, pp. 759-768.*
Van Der Klei et al., "Biosynthesis and assembly of alcohol oxidase, a peroxisomal matrix protein in methylotrophic yeasts: A review", Apr. 1991, Yeast, vol. 7, pp. 195-209.*
"Biochemistry, Second Edition," Voet and Voet, John Wiley and Sons, New York, 1995, p. 59.*
"Encyclopedia of Molecular Biology," Creighton, T., John Wiley and Sons, Inc. New York, 1999, pp. 586 and 2725.*
"Introduction to Protein Structure Second Edition," Branden and Tooze, Garland Publishing Inc., New York, 1999, pp. 374-375.*
"Principles of X-ray Crystallography," Drenth, Springer, New York, 1995, p. 1.*
Kierzek et al. (Biophys Chem 91:1-20.*
Wiencek (Ann Rev Biomed Eng 1:505-534.*
Aleshin et al. FEBS Lett 434:42-46, 1998.*
Borowski et al. Eur. J. Biochem. 266:715-723, 1999.*
Ford et al. Prot Exp Purif 2:95-107, 1991.*
Xiao et al. Cell 99:545-555, 1999.*
Kierzek et al. (Biophys Chem 91:1-20), 2001.*
Wiencek (Ann Rev Biomed Eng 1:505-534), 1999.*
Cho et al., "Crystal structure of RNA helicase from genotype 1b hepatitis C virus. A feasible mechanism of unwinding duplex RNA." *J Biol Chem.* Jun. 12, 1998; 273(24):15045-52.
de la Cruz et al., "Unwinding RNA in *Saccharomyces cerevisiae*: DEAD-box proteins and related families", *Trends Biochem Sci.* May 1999; 24(5):192-8. Review.
*Fields Virology*, 3rd Ed. (B.N. Fields et al., eds., Raven, New York, 1996) p. 615.
Gorbalenya et al., "A novel superfamily of nucleoside triphosphate-binding motif containing proteins which are probably involved in duplex unwinding in DNA and RNA replication and recombination." *FEBS Lett.* Aug. 1, 1988; 235(1-2):16-24. Review.
Gorbalenya and Koonin, "Helicases: amino acid sequence comparisons and structure-function relationships", *Current Opinion in Structural Biology*, 1993 3:419-429.
Grakoui et al., "Expression and identification of hepatitis C virus polyprotein cleavage products", *J Virol.* Mar. 1993; 67(3):1385-95.
Howe et al., "A novel recombinant single-chain hepatitis C virus NS3-NS4A protein with improved helicase activity", *Protein Sci.* Jun. 1999; 8(6):1332-41.
Jankowsky et al., "The DExH protein NPH-II is a processive and directional motor for unwinding RNA", *Nature.* Jan. 27, 2000; 403(6768):447-51.
Kadaré and Haenni, "Virus-encoded RNA helicases" *J Virol.* Apr. 1997; 71(4):2583-90. Review. No abstract available.

(Continued)

*Primary Examiner*—David J Steadman

(57) ABSTRACT

This invention provides fragments of HCV NS3 helicase, and crystalline compositions thereof, based on subdomains of HCV helicase protein. The protein fragments are stable, soluble, and structurally sound. They can be expressed at high levels in conventional expressions systems, such as *E. coli*, to permit efficient, large-scale production for NMR-based screening applications and production of $[^2H,^{13}C,^{15}N]$- and $[^{13}C,^{15}N]$-labeled polypeptides for structural NMR studies. Helicase fragments of the present invention are useful in the most advanced NMR techniques available, e.g., NMR-based drug discovery techniques such as SAR-by-NMR, in biological assays to discover inhibitors of HCV NS3 helicase, and to evaluate the mechanism of action and substrates for HCV NS3 helicase. Crystals of the present invention are useful for structure-based drug design studies using x-ray crystallographic techniques.

7 Claims, 3 Drawing Sheets

OTHER PUBLICATIONS

Kim et al., "Hepatitis C virus NS3 RNA helicase domain with a bound oligonucleotide: the crystal structure provides insights into the mode of unwinding", *Structure* 6(1):89-100 (1998).

Kim et al., "Towards defining a minimal functional domain for NTPase and RNA helicase activities of the hepatitis C virus NS3 protein", *Virus Res.* May 1997; 49(1):17-25.

Koonin and Dolja, "Evolution and taxonomy of positive-strand RNA viruses: implications of comparative analysis of amino acid sequences", *Crit Rev Biochem Mol Biol.* 1993; 28(5):375-430. Review. Erratum in: Crit Rev Biochem Mol Biol 1993; 28(6):546.

Korolev et al., "Comparisons between the structures of HCV and Rep helicases reveal structural similarities between SF1 and SF2 superfamilies of helicases", *Protein Sci.* Mar. 1998; 7(3):605-10.

Lohmann et al., "Processing pathways of the hepatitis C virus proteins", *J Hepatol.* 1996; 24(2 Suppl):11-9. Review.

Pause and Sonenberg, "Helicases and RNA unwinding in translation", *Curr Opin in Struct Biol* 3:953-959 (1993).

Shuker et al., "Discovering high-affinity ligands for proteins: SAR by NMR", *Science.* Nov. 29, 1996; 274(5292):1531-4.

Suzich et al., "Hepatitis C virus NS3 protein polynucleotide-stimulated nucleoside triphosphatase and comparision with the related pestivirus and flavivirus enzymes.", *J Virol.* Oct. 1993; 67(10):6152-8.

Yao et al., "Structure of the hepatitis C virus RNA helicase domain", *Nat Struct Biol.* Jun. 1997; 4(6):463-7.

\* cited by examiner

HEPATITIS C VIRUS NS3 HELICASE SUBDOMAIN I

This application claims priority from U.S. Provisional Patent Application No. 60/194,419, filed on Apr. 4, 2000, which is incorporated herein by reference in its entirety under 35 USC § 119(e).

FIELD OF THE INVENTION

The present invention relates to fragments of HCV NS3 RNA helicase, including mutants, homologues and co-complexes thereof, which are properly folded, soluble, monodisperse, and stable in buffered aqueous solutions at physiological pH (4-8). Helicase fragments of the invention maintain these properties at concentrations necessary to screen for and design specific inhibitors against HCV helicase using NMR, X-ray crystallographic and biological functional assay methods.

BACKGROUND OF THE INVENTION

The hepatitis C virus (HCV) causes one of the world's most pandemic and insidious diseases. According to the World Health Organization, there are approximately 170 million carriers worldwide with prevalence up to 0.5-10% [Release, Lancet, 351: 1415 (1998)]. In the United States, four million individuals are afflicted with hepatitis C [Alter and Mast, Gastroenterol Clin North Am, 23: 437-455 (1994)], of which 75% to 85% will develop a chronic infection. This may ultimately lead to cirrhosis (10% to 20%) and hepatocellular carcinoma (1% to 5%) [Cohen, Science, 285: 26-30 (1999)]. The causative agent, HCV, was identified in 1989 and accounted for 50% to 60% of the non-A, non-B transfusion associated hepatitis [Alter et al., N Engl J Med, 321: 1494-1500 (1989); Choo et al., Science, 244: 359-362 (1989); Kuo et al., Science, 244: 362-364 (1989)]. More than 100 strains of the virus have been identified, and are grouped into six major genotypes which tend to cluster in different regions of the world [Simmonds, Current Studies in Hematology and Blood Transfusion, Reesink, ed., Karger, Basel, pp. 12-35 (1994); van Doorn, J Med Vir, 43: 345-356 (1994)].

To date, interferon-alpha monotherapy and interferon-alpha-2b and ribavirin combination therapy (REBETRON® (combination therapy containing REBETOL® (ribavirin, USP) capsules and INTRON® A (interferon alpha-2b, recombinant) injection) Schering-Plough, Kenilworth, N.J.) are the only approved treatments. However, in one study less than 10% of the patients responded to interferon-alpha monotherapy and 41% of the patients responded to REBETRON® (combination therapy containing REBETOL® (ribavirin, USP) capsules and INTRON® A (interferon alpha-2b, recombinant) injection) [Reichard et al., Lancet, 351: 83-87 (1998)]. The most promising antiviral targets in chronic HCV infection are the replication enzymes, RNA-binding proteins, viral entry proteins and enzymes required for viral maturation. Therefore, it would be advantageous if those skilled in the art had the means to develop more effective antiviral agents against the various viral targets to effectively combat this disease.

HCV is a member of the Flaviviridae family. It is a positive-sense, single-stranded RNA virus with genome size of approximately 9.4 kb [Heinz, Arch Viral Supp, 4: 163-171 (1992); Mizokami and Ohba, Gastroenterol JPN, 28 Supp 5: 42-44 (1993); Ohba et al., FEBS Lett, 378: 232-234 (1996); Takamizawa et al., J Virol, 65: 1105-1113 (1991)]. HCV genomic RNA encodes a polyprotein of approximately 3000 amino acid residues: $_{NH_2}$-C-E1-E2-p7-NS2-NS3-NS4A-NS4B-NS5A-NS5B-$_{COOH}$ [Lohmann et al., J Hepatol, 24: 11-19 (1996); Simmonds, Clin Ther, 18 Supp B: 9-36 (1996)]. The polyprotein undergoes subsequent proteolysis by host and viral enzymes to yield mature viral proteins [Grakoui et al., J Virol, 67: 1385-1395 (1993); Shimotohno et al., J Hepatol, 22: 87-92 (1995)].

The NS3 protein has been the target of interest for antiviral discovery because of its important roles in HCV maturation and replication. There are two major functional domains: the amino-terminal one third of the protein is a serine protease responsible for certain key aspects of polyprotein processing [Shimotohno et al., J Hepatol, 22: 87-92 (1995)], and the carboxy-terminal two thirds shares sequence similarity with the DEAD box family of RNA helicases [Gorbalenya et al., FEBS Lett, 235: 16-24 (1988); Koonin and Dolja, Crit. Rev Biochem Mol, 28: 375-430 (1993); Korolev et al., Protein Science, 7: 605-610 (1998)].

RNA helicases are grouped into two major superfamilies (SFI and SFII) on the basis of the occurrence of seven conserved motifs, a smaller superfamily (SFIII), and two smaller families [Gorbalenya and Koonin, Curr Opin Struct Biol, 3: 419-429 (1993)]. RNA helicases are mostly of the SFII superfamily and can be further classified into families on the basis of particular consensus sequences in the conserved motifs [de la Cruz et al., TIBS, 24: 192-198 (1999)]. The HCV NS3 RNA helicase is classified as a DExH protein of the SFII superfamily. HCV helicase has two enzymatic activities: NTPase, which is believed to provide an energy source for the unwinding reaction through NTP hydrolysis, and nucleic acid unwinding [Kim et al., Virus Res, 49: 17-25 (1997); Suzich et al., J Virol, 67: 6152-6158 (1993)]. As such, HCV RNA helicase is essential for replication and production of infectious virions, which makes it an excellent target for therapeutics [Kadaré and Haenni, J Virol, 71: 2583-2590 (1997)]. Studies of the crystal structure of HCV helicase reveal that it has three subdomains: subdomain I, which contains NTP and $Mg^{++}$ binding sites; subdomain II, which is believed to contain a nucleic acid binding site; and subdomain III, which has an extensive helical structure. A coupling region lies between subdomains I and II, and is believed to be involved in transforming chemical energy into motion associated with unwinding [Kim et al., Structure, 156: 89-100 (1998); Cho et al., JBC, 273: 15045-15052 (1998); Yao et al., Nat StructBiol, 4: 463-467 (1997)]. The functions of some of these motifs have been elucidated by studies of the effects of mutations on NTP and RNA binding, NTP hydrolysis and unwinding activity [Pause and Sonenberg, Curr Opin Struct Biol, 3: 953-959 (1993)]. Recently, the basic mechanism for RNA duplex unwinding by the DExH RNA helicase NPH-II was described [Jankowsky et al., Nature, 403: 447-451 (2000)], however, in almost all cases the precise mechanism and the substrates of these enzymes have not been defined. Therefore, it would be beneficial to those skilled in the art to have suitable fragments of the HCV NS3 helicase which could be used to provide such valuable information and simplify the development of specific inhibitors for this enzyme. Nevertheless, there has been no report of an HCV helicase subdomain or fragment that is suitable for this purpose.

To better study the enzymatic properties of the HCV NS3 helicase (e.g., NTP binding, single and double stranded nucleic acid binding sites, energy coupling and helicase activity) and develop potential inhibitors against this enzyme, it is desirable to have suitable fragments of the protein for use in methods or techniques such as nuclear magnetic resonance (NMR) spectroscopy and X-ray crystallography. For example, recent developments in NMR-based drug discovery methods provide a powerful means for identifying and optimizing non-peptide drug-like leads, however, such methods are currently limited to proteins having a size of about less than 30 kDa [Shuker et al., *Science*, 274: 1531-1534 (1996)] and smaller helicase fragments have not been previously reported. The 451 residue HCV NS3 helicase, which is about 48.2 kDa, is simply too large for effective use in such methods. Furthermore, to be useful, a fragment should be folded correctly, soluble, monodisperse, and stable in a buffered aqueous solution close to physiological conditions (pH 4-8 and salt concentrations less than about 250 mM). Therefore, it would be advantageous to have fragments of HCV NS3 helicase that are suitable for the most advanced techniques for characterizing proteins and designing inhibitors such as NMR, X-ray crystallography and ATPase assays such as the continuous spectrometric assay [Pullman et al., *J Biol Chem*, 235: 3322-3329 (1960)]. In addition, such fragments should be suitable for probing NTP and nucleic acid binding sites of the HCV NS3 helicase by NMR and crystallography, which together with mechanistic studies will provide insights into the mode of unwinding for HCV helicase.

SUMMARY OF THE INVENTION

The present invention provides novel fragments of HCV NS3 helicase based on the three subdomains I, II, and III. The fragments are properly folded, soluble at millimolar concentrations, monodisperse, and stable in buffered aqueous solutions under physiological conditions (pH 4-8). In addition, the fragments are small (less than about 30 kDa), making them useful for NMR-based drug discovery techniques (compared to the full length enzyme which is too large for this purpose). The solubility and stability of HCV helicase fragments of this invention are easily optimized, as needed, by varying solution conditions and/or by introducing additional specific mutations into the fragment, as described. The properties of an HCV NS3 helicase fragment of the invention allows it to be expressed at high levels in conventional expressions systems, such as *E. coli*, to permit efficient, large-scale production, e.g., as [$^{15}$N]-labeled polypeptide for NMR-based screening applications and production of [$^2$H,$^{13}$C,$^{15}$N]- or [$^{13}$C,$^{15}$N]-labeled polypeptide for structural NMR studies. Thus, the properties of a fragment makes it useful in the most advanced NMR techniques available, e.g., novel NMR-based drug discovery techniques such as SAR-by-NMR [see, e.g., Shuker et al., *Science*, 274: 1531-1534 (1996) and U.S. Pat. No. 5,989,827], in biological functional assays to discover inhibitors of HCV NS3 helicase, and to evaluate the mechanism of action and substrates for HCV NS3 helicase.

The invention further relates to HCV NS3 helicase fragments in crystalline form, and to conditions for crystallizing the same. A crystalline helicase fragment of the invention is useful in X-ray crystallography to identify non-peptide drug-like small molecule inhibitors of HCV NS3 helicase based on the crystalline structure (including homologues, mutants, and co-complexes of crystalline fragments). By detecting the interactions between an inhibitor and cyrstalline helicase fragment, the activity of such inhibitors can be further optimized.

Helicase fragments and crystals of this invention are also useful for probing NTP and nucleic acid binding sites of HCV NS3 helicase using NMR spectroscopy and X-ray crystallography techniques, which, together with mechanistic studies, provide insight into the mode of unwinding for HCV helicase.

Helicase fragments and crystals of this invention also provide methods for determining the three-dimensional structure (coordinates and atomic details) of such helicase fragments, or mutants, homologues or co-complexes thereof, in order to design, computationally evaluate, synthesize and use inhibitors of HCV NS3 helicase which may prevent or treat the undesirable physical and pharmacological properties of HCV.

Thus, in one embodiment, the invention provides fragments of HCV NS3 protein which are derived from amino acids 181 to 324; from amino acids 327 to 481, wherein the amino acid residues at positions 431 to 451 are deleted and replaced by the amino acid sequence SDGK (SEQ ID NO: 2); from amino acids 181 to 481, wherein the amino acid residues at positions 431 to 451 are deleted and replaced by amino acids SDGK (SEQ ID NO: 2); and from amino acids 181 to 572, wherein the amino acid residues at positions 328 to 482 are deleted.

In another embodiment, the invention provides buffered solutions, which contain from 50 to 1000 µM of a helicase fragment, from 5 to 15% weight to volume of $D_2O$, a protease inhibitor, 25 to 250 mM $KPO_4$, and 1 to 10 mM DTT, wherein the pH of the solution is from about 4 to 8.

The invention further provides precipitant solutions which contain from 1 to 60 µg of a helicase fragment, from 5 to 40% weight to volume of a precipitant compound, from 1 to 1000 mM of a salt, and a buffer for a precipitant solution, wherein the pH of the solution is from about 4 to 8 and the temperature is from about 1 to 26° C.

In still another embodiment, the invention provides methods for identifying inhibitor compounds of HCV helicase protein, which may include obtaining a helicase polypeptide fragment, which comprises a subdomain I or subdomain II, and contacting the fragment with a potential inhibitor compound; assaying the fragment in contact with the inhibitor compound and the HCV helicase protein for activity based on the subdomain; and comparing the activity of the fragment in contact with the compound to the activity of the HCV helicase protein, such that a decrease in the activity of the fragment compared with the HCV helicase protein identifies the compound as an inhibitor of HCV helicase activity. Alternatively, the activity of a helicase fragment, which is not in contact with an inhibitor compound, can be compared with the activity of a fragment in contact with the compound, instead of a full-length helicase protein.

These and other embodiments of the invention will be appreciated by considering the following detailed description of the invention and the accompanying Examples.

DETAILED DESCRIPTION OF THE INVENTION

Figure 1A:
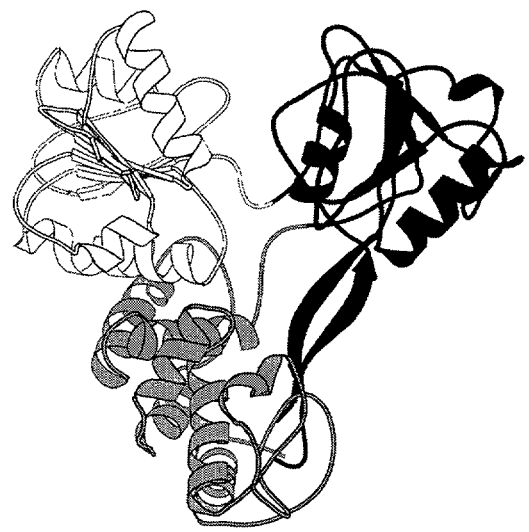
FIG. 1A depicts a ribbon diagram of an HCV NS3 RNA helicase. Subdomains I, II, and III are shown in white, black, and gray, respectively.

All references cited herein are hereby incorporated by reference in their entireties.

Molecular Biological Techniques and Definitions

In accordance with the present invention, there may be employed conventional molecular biology, microbiology, or recombinant DNA techniques within the ordinary skill of the art to prepare viral constructs and helicase fragments of the invention. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D.N. Glover ed. 1985); *Oligonucleotide Synthesis* [M. J. Gait ed. (1984)]; *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; *A Practical Guide To Molecular Cloning* [B. Perbal (1984)]; *Current Protocols in Molecular Biology*, John Wiley & Sons, Inc. [F. M. Ausubel et al. (eds.) (1994)]; [Burleson, *Virology: A Laboratory Manual*, Academic Press, New York (1992)].

As used herein, the abbreviations "nt" and "aa" refer to "nucleotide(s)" and "amino acid(s)", respectively.

A "nucleic acid molecule" refers to the phosphate diester polymeric form of ribonucleosides (adenosine, guanosine, uridine or cytidine; "RNA molecules"), or deoxyribonucleosides (deoxyadenosine, deoxyguanosine, deoxythymidine, or deoxycytidine; "DNA molecules"), in either a single stranded or a double stranded form. Double stranded DNA-DNA, DNA-RNA and RNA-RNA helices are contemplated. The term nucleic acid molecule, and in particular DNA or RNA molecule, refers only to the primary and secondary structure of the molecule, and does not limit it to any particular tertiary forms. The structure of a particular nucleic acid molecule, sequence or region may be described herein according to the normal convention of providing a sequence in the 5' to 3' direction. A "recombinant" DNA molecule has undergone a molecular biological manipulation.

The term "gene" means a DNA sequence that encodes or corresponds to a particular sequence of amino acids, which comprise all or a portion of one or more proteins or enzymes. Preferably, if a gene encodes only a portion or fragment of a protein or enzyme, then it encodes a functional portion (e.g., a subdomain) that has an activity present in the full length protein or enzyme. For example, a viral gene encoding an HCV NS3 helicase may encode the entire helicase domain or it may encode a fragment thereof.

A "subdomain" refers to a segment of amino acids of a protein or polypeptide that has a particular property, e.g., nucleic acid unwinding activity, NTPase activity or ATP binding or catalytic activity. "Subdomain I" refers to a fragment of HCV NS3 which corresponds to aa 181 to 327; "subdomain II" refers to a fragment of HCV NS3 which corresponds to aa 328 to 483; "subdomain III" refers to a fragment of HCV NS3 which corresponds to aa 484 to 631.

A "fragment" refers to a segment of amino acids derived from an HCV NS3 helicase protein. A fragment preferably includes a subdomain or a fragment thereof, but may also comprise an entire domain. An HCV helicase fragment of the present invention has a molecular mass (size) between about 5 and 30 kDa, which can be assessed using conventional techniques in the art, e.g., SDS PAGE. The smaller size allows effective use with the most advanced NMR methods. Modification(s) to fragments of the present invention (e.g., variants) are contemplated and described in greater detail below.

"Monodisperse" and "predominantly uniform molecular species", in reference to an HCV helicase fragment of the present invention, can be used interchangeably to indicate that the mean radius of particles comprising the HCV helicase fragment varies by less than 30%, preferably less than 15%, as determined by, e.g., conventional dynamic light scattering methods. A monodisperse helicase fragment in solution preferably exists in a monomeric form, however, oligomers (e.g., dimers, trimers tetramers, etc.) may exist too. Such oligomeric forms of a helicase fragment preferably have a molecular weight of less than about 30 kDa.

As used herein, "helicase fragment" or "helicase protein", refer to a polypeptide derived from an HCV NS3 gene, e.g., HCV-1a NS3 [Rice, in *Fields Virology*, 3$^{rd}$ ed. (B. N. Fields et al., eds., Raven, N.Y.) p. 615 (1996); SEQ ID NO: 1], which polypeptide exhibits one or more properties of HCV NS3 helicase activity. A helicase fragment preferably lacks any portion of HCV NS3 that exhibits protease activity, e.g., that portion of the HCV NS3 protease located in aa 1 to 180 of SEQ ID NO: 1. A helicase fragment of this invention is (1) structurally sound (i.e., it folds properly in comparison with a full length HCV NS3 helicase protein based on NMR or crystallography studies), (2) soluble (i.e., it folds properly upon expression such that the polypeptide fragment does not form inclusion bodies, aggregate, or require the use of a solvent or other reagent to induce the proper folding of the enzyme in comparison with the full length helicase protein), (3) stable in a buffered solution (e.g., the protein maintains a conformation that is properly folded in buffered solutions, which can be used for NMR or crystallography applications, in comparison with the full length HCV helicase protein, for a period of time needed to perform the NMR or x-ray crystallography study, typically for at least two weeks), and (4) monodisperse (i.e., it exists as a predominantly uniform molecular species in solution where the size of the uniform molecular species is suitable for NMR and x-ray crystallography studies).

A "sequence-conservative variant" of a gene contains a change of one or more nucleotides in a given codon position, which results in no alteration in the amino acid encoded at that position. A "function-conservative variant" contains a change to one or more nucleotides which causes an alteration in an amino acid residue in the protein or enzyme, including, but not limited to replacement of an amino acid for another having similar properties (such as, for example, polarity, hydrogen bonding potential, acidic, basic, hydrophobic, aromatic, and the like). The resulting amino acid in a function-conservative variant does not alter the overall conformation or function of the polypeptide.

A "coding sequence" or a sequence "encoding" an expression product, e.g., RNA, polypeptide, protein, or enzyme, is a nucleotide sequence that, when expressed, results in the production of that expression product. A coding sequence is "under the control" or "operatively associated with" transcriptional and translational control sequences in a cell when an RNA polymerase transcribes the coding sequence into mRNA, which can then be translated into a protein encoded by the coding sequence.

The terms "express" and "expression" mean allowing or causing the information in a gene or DNA sequence to become manifest, e.g., producing a protein by activating the cellular functions involved in transcription and translation of a corresponding gene or DNA sequence. A DNA sequence can be expressed using in vitro translation assays or in or by a cell to form an "expression product" such as a mRNA or a protein. The expression product, e.g. the resulting protein, may also be referred to as "expressed".

Subdomains of HCV NS3 Helicase

The 451 residue helicase of HCV NS3 has three nearly equal-sized subdomains, which form a triangular-shaped molecule approximately 65 Å on a side and 35 Å thick (see FIG. 1A). Subdomains I and III share a more extensive interface together than either shares with subdomain II. Therefore, the amino- and carboxy-terminal subdomains are closely packed and form a rigid unit, whereas the second subdomain is flexibly linked to the remainder of the structure and can rotate as a rigid body.

Figure 1B:
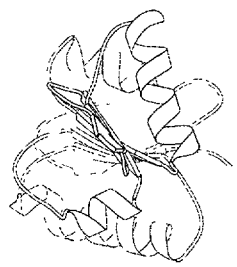
FIG. 1B depicts a ribbon diagram of an HCV NS3 helicase subdomain I construct (SEQ ID NO: 3) containing residues 181-324 from HCV-1a NS3 helicase.

In one embodiment of the invention, fragments are based on subdomain I of HCV NS3 helicase, i.e., the "NTPase subdomain" which includes NTP-binding residues (aa 181 to 327 of SEQ ID NO: 1) within the nucleotide binding fold shared by other NTPases (FIG. 1B). Thus, fragments of subdomain I can be prepared, e.g., from aa 181 to 324 of SEQ ID NO: 1, using conventional molecular biology cloning techniques. A fragment is exemplified by SEQ ID NO: 3, however variants are contemplated as described in greater detail below, e.g., a polypeptide fragment of aa 190 to 327 of SEQ ID NO: 1 would be functional. Assays for determining NTPase activity of helicases are well known in the art, and such assays are contemplated for determining activity of a helicase fragment of subdomain I in the absence or presence of inhibitor compounds [see, e.g., Howe et al., *Protein Science*, 8: 1332-1341 (1999) for discussion of helicase protein activity assays].

Higher concentrations of fragments derived from subdomain I (about 1 mM) can be prepared without aggregation of polypeptides by making additional substitutions within this subdomain. Such an improvement in the solubility of fragments derived from subdomain I, at higher protein concentrations, is beneficial for NMR-based drug discovery techniques (see, e.g., U.S. Pat. No. 5,989,827), since aggregation will interfere with NMR techniques. Thus, to further improve the solubility and maintain the desirable monomeric state of fragments of the present invention, fragments derived from HCV helicase subdomain I that are desirable at higher concentrations can be prepared with an amino acid substitution at either aspartic acid (Asp) 249 or arginine (Arg) 257. Substitutions to both residues in the same polypeptide fragment will likely not improve the solubility of the fragment. Amino acid residues that can be employed for substitution include non-polar amino acids, e.g., alanine, valine, leucine, isoleucine, and phenylalanine. The preferred substitutions for aspartic acid 249 include lysine and arginine. The preferred substitutions for arginine 257 include glutamic acid and aspartic acid.

Figure 1C:
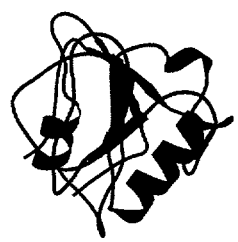
FIG. 1C depicts a ribbon diagram of an engineered HCV NS3 helicase subdomain II construct (SEQ ID NO: 4) containing residues 327-481 from HCV-1a NS3 helicase, in which residues 431-451 are replaced by the tetra-peptide insertion SDGK (SEQ ID NO: 2) at residue 431.

Fragments of the invention are also based on subdomain II of HCV NS3 helicase, i.e., the "RNA binding subdomain" which includes an Arg-rich (aa 460 to 468) sequence that is required for RNA unwinding. Fragments of subdomain II can be prepared, e.g., from aa 327 to 481 of SEQ ID NO: 1, using conventional molecular biology cloning techniques. A fragment based on subdomain II is exemplified by SEQ ID NO: 4 (see also FIG. 1C), however variants are contemplated as described in greater detail below, e.g., a polypeptide fragment of aa 327 to 489 of SEQ ID NO: 1 would also be functional. Assays for determining RNA binding kinetics of helicases are well known in the art, and such assays are contemplated for determining activity of a helicase fragment of subdomain II in the absence or presence of inhibitor compounds [see, e.g., Howe et al., *Protein Sciences*, 8: 1332-1341 (1999) for discussion of helicase protein activity assays].

Fragments of the invention comprising subdomain II can be improved, e.g., have better folding properties, by reducing the size of an antiparallel β-loop at aa 431 to 451. Hydrophobic patches of residues may contribute to formation of inclusion bodies or to aggregation of polypeptides containing this subdomain. Using the sequence of SEQ ID NO: 1 as an example, it is preferred that at least residue 438 is removed from a fragment including subdomain II, more preferably residues 431 to 451 are removed. Shorter or longer deletions carboxy-terminal or amino-terminal to residues 431 to 451 are permissible as needed, but in any case should not exceed residues 430 to 452. Engineered loops can be constructed by deleting residues in the amino-terminal portion of subdomain II (e.g., aa 430-438), and in the carboxy-terminal portion (e.g., aa 444-452) followed by insertion of linkers containing two to six residues. An insertion to replace the antiparallel β-loop of subdomain II can significantly improve the solubility and stability of an HCV helicase fragment of the invention containing this subdomain. It is preferred that amino acid sequence SDGK (SEQ ID NO: 2) is inserted for deletions of the antiparallel β-loop. Other possible insertions include QGGA (SEQ ID NO: 7), RGST (SEQ ID NO: 8), RGPG (SEQ ID NO: 9), SKGE (SEQ ID NO: 10), EQGA (SEQ ID NO: 11), RNNQ (SEQ ID NO: 12), ADGS (SEQ ID NO: 13), and CDGL (SEQ ID NO: 14). Examples of these fragments are provided by SEQ ID NOS: 4 and 5.

Fragments can also be prepared from subdomains III of HCV NS3 helicase, i.e., the "α-helical subdomain", which can be derived from aa 484 to 631 of SEQ ID NO: 1.

Figure 1D:
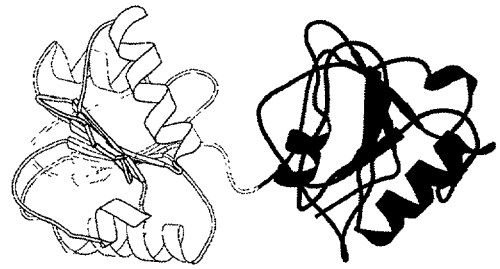
FIG. 1D depicts a ribbon diagram of an engineered HCV NS3 helicase subdomain I,II construct (SEQ ID NO: 5) containing residues 181-481 from HCV-1a NS3, in which residues 431-451 are replaced by the tetra-peptide insertion SDGK (SEQ ID NO: 2) at residue 431. Subdomains I and II are shown in white and black, respectively.
Figure 1E:
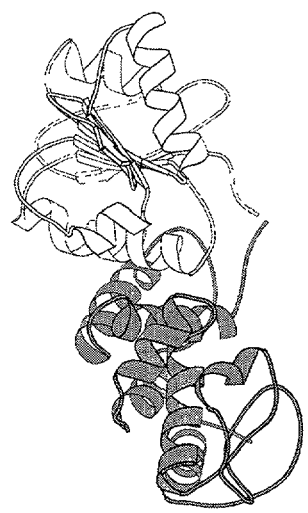
FIG. 1E depicts a ribbon diagram of an engineered HCV NS3 helicase subdomain I,III construct (SEQ ID NO: 6) containing residues 181-572 from HCV-1a NS3, in which residues 328-482 are deleted. Subdomains I and III are shown in white and gray, respectively.
Figure 2:
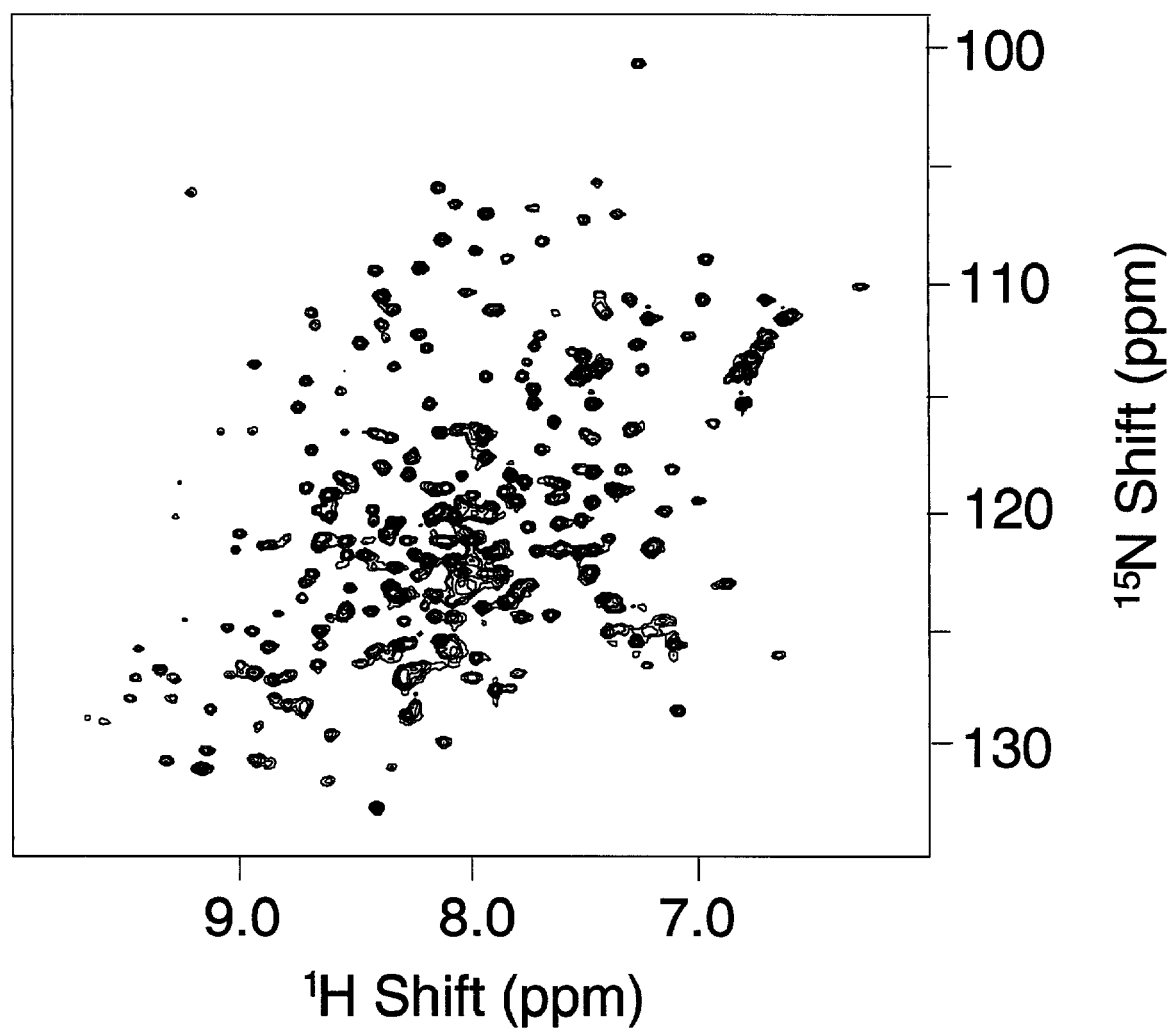
FIG. 2 depicts a two dimensional (2D) $^{15}$N-HSQC NMR spectrum of 200 μM HCV NS3 helicase subdomain I,II construct (SEQ ID NO: 5).

Fragments, which include combinations of segments from different subdomains of HCV NS3 helicase, are also contemplated. For example, fragments of the invention can be prepared from subdomains I and II, I and III, or II and III. In a specific embodiment described in the Examples below, fragments are prepared from subdomains I and II (e.g., SEQ ID NO: 5; FIG. 1D) and subdomains I and III (e.g., SEQ ID NO: 6; FIG. 1E).

Fragments of the invention which are based on subdomains I and II can be prepared, e.g., from aa 181 to 483 of HCV-1a NS3, using conventional molecular biological techniques and the rationale set forth above for preparing fragments based on subdomains I and II individually.

Inspection of the three-dimensional structure of the HCV NS3 helicase reveals that the carboxy-terminus of subdomain I and the amino-terminus of subdomain III are very close to each other (approximately 4 Å) in tertiary structure. Subdomains I and III can be linked by removing all residues of subdomain II, e.g., aa 328 to 482 of HCV-1a NS3. Removal of subdomain II reduces the molecular weight of a full-length helicase domain by about 15 kDa. To further reduce the molecular weight of fragments that include subdomains I and III, up to an additional 59 residues can be deleted from the carboxy-terminus of subdomain III (aa 573 to 631) based on a deletion mutation study. In fragments containing subdomain I and truncated subdomain III, both a specific nucleic acid binding pocket and the ATP binding pocket are preserved (see FIG. 1E).

Variants of HCV Helicase Fragments

A polynucleotide encoding a helicase fragment of the present invention can differ in nucleotide sequence from another reference polynucleotide encoding the same fragment, e.g., helicase from HCV-1a versus helicase from HCV-1b. A change in the nucleotide sequence of the variant may be silent, i.e., it may not alter an amino acid encoded by the polynucleotide. Where an alteration is limited to a silent change of this type a variant will encode a polypeptide with the same amino acid sequence as the reference polypeptide (i.e., sequence-conservative variant). Changes in the nucleotide sequence of the variant may alter the amino acid sequence of the polypeptide encoded by the reference polynucleotide in its nucleotide or amino acid sequence, as described below. Thus, an HCV NS3 helicase polypeptide fragment of the invention can differ in amino acid sequence from another reference HCV NS3 helicase polypeptide fragment of the invention, i.e., a variant. A "variant" can be a polynucleotide or polypeptide that differs from a reference polynucleotide or polypeptide, respectively. Such variants of a helicase fragment of the invention, as described herein, are contemplated for use in various assays and biological techniques such as NMR and crystallography in a similar manner as described for the non-variant helicase fragment.

As used herein, the "reference" polynucleotide or protein is derived from HCV-1a for purposes of example. Since fragments of the invention are derived from strains/isolates of HCV, differences in amino acid sequences of NS3 helicase are limited so that the sequences of the reference and the variant are closely similar overall and identical in many regions. A variant and reference polypeptide may differ in amino acid sequence by one or more mutations, substitutions, additions, deletions, truncations (deletion of residues from the amino-terminus, carboxy-terminus or both), fusion proteins or synthetic changes, e.g., pegylation. Such modifications, which may be present in any combination, are well known in the art and discussed in greater detail below.

A variant may have (i) one or more amino acid residues substituted with a conserved or non-conserved amino acid residue (preferably a conserved amino acid residue, e.g., Gly/Ala, Asp/Glu, Val/Ile/Leu, Lys/Arg, Asn/Gln and Phe/Trp/Tyr) and such substituted amino acid residue may or may not be encoded by the genetic code, or (ii) one or more amino acid residues that includes a substituent group resulting in a natural or non-naturally occurring amino acid, e.g., aliphatic esters or amides of the carboxy-terminus or of residues containing carboxyl side chains, O-acyl derivatives of hydroxyl group-containing residues, and N-acyl derivatives of the amino-terminal amino acid or amino-group containing residues (e.g. lysine or arginine), phosphorylated amino acid residues (e.g., phosphotyrosine, phosphoserine or phosphothreonine), sulfonation, biotinylation, or (iii) a mature polypeptide that is fused with another compound, such as a compound to increase the half-life of the polypeptide (for example, polyethylene glycol), or (iv) additional amino acids not derived from HCV helicase fused to the mature polypeptide (i.e., a fusion protein), such as a leader or secretory sequence or a sequence which is employed for purification of the mature polypeptide or a pro-protein sequence. A fragment of the invention may further have combinations of these modifications.

If a fusion protein is desirable, the HCV NS3 helicase fragment can be either at the amino or carboxy termini of the fusion protein. Suitable functional enzyme fragments are polypeptides that exhibit a quantifiable activity when expressed fused to the HCV NS3 helicase fragment. Exemplary enzymes include, without limitation, β-galactosidase (β-gal), β-lactamase, horseradish peroxidase (HRP), glucose oxidase (GO), human superoxide dismutase (hSOD), urease, and the like. These enzymes are convenient because the amount of fusion protein produced can be quantified by means of simple colorimetric assays. Alternatively, one may employ fragments or antigenic proteins, to permit simple detection by metal-binding columns and quantification of fusion proteins using antibodies specific for the fusion partner. A histidine tag of six histidine residues at a terminus of a fragment of the invention, preferably at the amino terminus, allows easy purification of fragments using methods well known in the art.

Still other modifications can be prepared by the use of agents known in the art for their usefulness in cross-linking proteins through reactive side groups. Preferred derivatization sites with cross-linking agents are free amino groups, carbohydrate moieties and cysteine residues.

Preparation of Helicase Fragments

Various pathogenic and attenuated strains of HCV are known in the art [see Lohmann et al., *J Hepatol*, 24: 11-19 (1996); Rice, in *Fields Virology*, 3$^{rd}$ ed. (1996), B. N. Fields et al., eds., Raven, N.Y., p. 615], and can be used to prepare a helicase fragment of the invention. Fragments can be prepared from a purified, naturally occurring form of an HCV NS3 or a recombinant form having a natural or engineered modification, e.g., substitution, deletion, insertion, inversion, or other change resulting in a variant, that may change a characteristic of HCV NS3 helicase fragment or have no observable effect. One or more amino acid changes to an HCV NS3 helicase fragment of the invention that results in a sequence- or function-conservative variant is contemplated by the invention.

Helicase fragments can also be prepared synthetically, based on the sequences disclosed herein (e.g., aa 181-631 of SEQ ID NO: 1, which sets forth the helicase domain of HCV-1a) using a variety of techniques well known in the art, e.g., chemical synthesis, site-directed mutagenesis [Gillman et al., *Gene*, 8: 81 (1979); Roberts et al., *Nature*, 328: 731 (1987); Innis, in *PCR Protocols: A Guide to Methods and Applications*, Academic Press, New York, N.Y. (1990)], polymerase chain reaction methods, automated obligonucleotide synthesis [e.g., see Warner, *DNA*, 3: 401 (1984)], and polypeptide synthesis (Atherton et al., in *Solid Phase Peptide Synthesis. A Practical Approach*, 1989, IRL Press, Oxford). Adding epitope tags for purification or detection of recombinant products is also contemplated. In a particular embodiment, described infra, a His tag is used in the preparation of fragments of the invention.

Conventional molecular biology and virology techniques can be used to obtain HCV strains/isolates, e.g., from a partial genomic sequence of a known strain, e.g., HCV-1a or HCV-1b [Rice, C. M., in *Fields Virology*, 3$^{rd}$ ed. (B. N. Fields et al., eds.), p. 615 (1996)]. A nucleic acid encoding HCV NS3 helicase domain can be prepared from any available strain/isolate of HCV and a fragment generated therefrom. To facilitate the teaching of the invention, fragments are described using the amino acid sequence of HCV NS3 derived from HCV-1a strain (SEQ ID NO: 1) by way of example. It shall be appreciated that other strains of HCV, which may have a helicase domain that is not identical to HCV-1a (e.g., a helicase variant) can be used to prepare fragments of the invention.

Expression systems

Various conventional expression systems can be employed to express an HCV NS3 helicase fragment of the invention, including prokaryotic (e.g., bacterial), eukaryotic (e.g., mammalian, yeast, and insect), and cell-free in vitro systems, which are commonly known in the art. To prepare HCV NS3 helicase fragments, conventional molecular biology techniques can be used to subclone HCV NS3 helicase polynucleotide encoding a fragment into a suitable expression vector, which is transformed into a suitable host and the fragment coding sequence expressed. For detailed methodologies see e.g., Sambrook supra. Preparation of helicase fragments for use in expression vectors is described in specific embodiments set forth in the Examples, infra. It is noted that the present invention is not limited to use of any particular vector or methodology described in the Examples below, which are provided for purposes of further illustrating the invention.

Both prokaryotic and eukaryotic host cells can be used to express a desired HCV NS3 helicase coding sequence when appropriate control sequences compatible with the selected host are used. Among prokaryotic hosts, E. coli is advantageous and preferred for expression of HCV NS3 helicase fragments because bacteria are easier to manipulate and higher quantities of protein expression can be achieved than with other available expression systems.

Cloning and expression vectors suitable for the needs of the practitioner can be selected from various, commercially available vectors that are compatible with prokaryotic hosts, e.g., pBR322, pUC, pET, and which also contain marker sequences conferring antibiotic resistance. The foregoing systems are particularly compatible with E. coli. Other prokaryotic hosts, e.g., strains of Bacillus and Pseudomonas, can be used with compatible control sequences known to those of ordinary skill in the art. In specific embodiments, described infra, the vector pET28b(+) (Novagen, Madison, Wis.) is used to express HCV NS3 helicase fragments. It is noted that due to a subcloning artifact from pET28b(+), these constructs have a G-S-H-M polypeptide sequence (residues 1-4 of SEQ ID NO:4) at the amino-temminus. Numerous expression control sequences are available for prokaryotes, including promoters, optionally containing operator portions, and ribosome binding sites, e.g., T7 bacteriophage promoter [Dunn and Studier, *J Mol Biol*, 166: 477 (1983)], β-lactamase (penicillinase) and lactose promoter systems [Chang et al, *Nature*, 198: 1056 (1977)], tryptophan (trp) promoter system [Goeddel et al., *Nuc Acids Res*, 8: 4057 (1980)], λ-derived $P_L$ promoter and N gene ribosome binding site [Shimatake et al., *Nature*, 292: 128 (1981)] and hybrid tac promoter [De Boer et al., *Proc Nat Acad Sci* USA, 292: 128 (1983)].

Eukaryotic hosts can be used as desired, including without limitation, yeast (e.g., Saccharomyces, Klebsiella, Picia, and the like) and mammalian cells in culture systems. Yeast-compatible vectors and control sequences are well known in the art and can carry markers that permit selection of successful transformants by conferring prototrophy to auxotrophic mutants or resistance to heavy metals on wild-type strains. Mammalian cell lines available as hosts for expression are known in the art and include many immortalized cell lines available from the American Type Culture Collection® (ATCC®) organization, including HeLa cells, Chinese hamster ovary (CHO) cells, baby hamster kidney (BHK) cells, and a number of other cell lines. Suitable promoters for mammalian cells are also known in the art, and include viral promoters from, e.g. Simian Virus 40 (SV40) [Fiers et al., *Nature*, 273: 113 (1978)], Rous sarcoma virus (RSV), adenovirus (ADV), and bovine papilloma virus (BPV), glyceraldehyde-3 phosphate dehydrogenase (GAPDH) promoter or alcohol dehydrogenase (ADH) regulatable promoter, terminators also derived from GAPDH, and if secretion is desired, a leader sequence derived from yeast α-factor (see U.S. Pat. No. 4,870,008). Mammalian cells may also require or benefit from terminator sequences, e.g., derived from the enolase gene [Holland, *J Biol Chem*, 256: 1385 (1981)], and poly-A addition sequences, enhancer sequences (which increase expression), sequences which promote gene amplification, e.g., methotrexate resistance genes, which are known in the art.

Transformation of a host cell with a vector containing a polynucleotide sequence encoding an HCV NS3 helicase subdomain is accomplished using known methods in the art for introducing nucleic acid into cells, and will typically depend upon the host to be transformed, [see, e.g., Cohen, *Proc Nat Acad Sci* USA, 69: 2110 (1972); Hinnen et al., *Proc Nat Acad Sci* USA, 75: 1929 (1978); Graham and Van der Eb, *Virol*, 52: 546 (1978)].

Isolation and Purification of Expressed HCV NS3 Helicase Fragments

After expression of an HCV NS3 helicase fragment, HCV NS3 helicase polypeptide fragments can be isolated and purified according to conventional methods in the art, typically depending upon the type of expression system used. In specific embodiments, illustrated infra, HCV NS3 helicase fragments are expressed from pET28b(+) in *E. coli* and isolated by lysing cells and centrifuging to obtain the supernatant which contains the HCV NS3 helicase fragment. The supernatant is subjected to $Ni^{2+}$ chelation chromatography to purify the fragment, which binds to the column due to the presence of an amino-terminal His tag on the fragment. The isolated fragment is then proteolytically cleaved with thrombin to remove the histidine tag. These fragments have a four residue sequence G-S-H-M (residues 1-4 of SEQ ID NO:4) at the amino terminus, which does not effect the function of the fragments. After thrombin proteolysis, the fragment of interest are separated from the histidine tag, e.g., by size exclusion chromatography.

ATPase Assay

ATPase assays can be performed to determine steady state kinetic parameters of HCV helicase using helicase fragments that contain at least subdomain I, such as by a continuous spectrophotometric assay [Pullman et al., *J Biol Chem*, 235: 3322-3329 (1960)]. Such an assay is also useful for comparing the ATPase activity of a fragment that is bound to or in a complex with an inhibitor compound with the activity of a full-length helicase protein or fragment not bound to an inhibitor.

Initial ATPase rates can be measured at constant ATP concentrations without accumulation of ADP product (e.g., using a fragment based on subdomains I,II versus subdomain I or subdomain I,III). ATPase catalyzed adenosine diphosphate (ADP) formation is coupled to oxidation of NADH by the enzymes pyruvate kinase (PK) and lactate dehydrogenase (LD) and an excess concentration of the intermediate substrate phospho(enol)pyruvate (PEP). The assay permits ATPase rates to be monitored by the change in absorption at 340 nm.

NMR Sample Preparation and NMR Characterization

Purified protein fragment samples, e.g. by gel filtration, can be concentrated to a desired concentration for NMR experiments (from about 50 to 1000 μM helicase, preferably about 200 μM) plus about 5 to 15% $D_2O$ (preferably about 10%), and conventional protease inhibitors, e.g., aprotinin, leupeptin, AEBSF [4-(2-Aminoethyl)-benzenesulfonyl fluoride], and Protease Inhibitor Cocktail I (Calbiochem, San Diego, Calif.), wherein the pH is pH 4 to 8.0, preferably pH 6 to 7. Alternatively, a buffer other than a gel filtration buffer can be used and exchanged using a desalting column, e.g., 25 to 250 mM $KPO_4$ (preferably 75 mM), 25 to 250 mM NaCl (preferably 50 mM), 1 to 10 mM DTT (preferably about 5 mM), 0.010 to 0.020% $NaN_3$ (preferably 0.015%), wherein the pH is adjusted to about 6.5. The protein solutions are then transferred into NMR tubes for NMR studies. Two-dimensional $^{15}$N-HSQC NMR spectra of the [$^{15}$N]-labeled HCV NS3 helicase fragments are acquired at 25° C. to assess the folding and stability of the fragments. The number of peaks and their dispersion in the 2D $^{15}$N-HSQC NMR spectra are indicative of fully folded proteins. The line widths of the peaks in the NMR spectra should be consistent with the molecular weight of the various HCV NS3 helicase fragments to indicate a fragment is monomeric under the conditions tested.

A preferred buffer for use in NMR for fragments of the invention includes 50 to 1000 μM of a helicase fragment, from 5 to 15% weight to volume of $D_2O$, a protease inhibitor, 25 to 250 mM $KPO_4$, and 1 to 10 mM DTT, wherein the pH of the solution is from about 4 to 8. Additional components, including 25 to 50 mM NaCl (preferably aobut 50 mM) and 0.010 to 0.02% $NaN_3$ (preferably about 0.015%), may be added to this buffer to enhance the unique properties of helicase fragments.

NMR Titration Experiments to Determine Binding of Adenosine Triphosphate (ATP)

Binding of adenosine triphosphate (ATP) to HCV NS3 helicase subdomain constructs can be determined using standard NMR titration experiments [Lian and Roberts, in *NMR of Macromolecules*, (Roberts, E. D., ed.) Oxford University Press, pp. 153-182 (1993)]. Such experiments are well suited for determining the interaction site of ligands with proteins and allow determination of dissociation constants of weak molecular interactions ($K_d>1$ μM). Known amounts of ATP are added incrementally to NMR samples of [$^{15}$N]-labeled HCV NS3 helicase subdomain constructs of known concentration. Two dimensional $^{15}$N-HSQC NMR spectra are collected after each addition of ATP. The dissociation constant ($K_d$) of ATP is derived from an analysis of the changes in amide chemical shifts of residues in the binding site of the protein as a function of the concentration of ATP.

NMR Resonance Assignments and Secondary Structure Determination

In the initial stage of any investigation by NMR spectroscopy, each nuclear magnetic resonance must be associated with a specific nucleus in the protein under investigation. Resonance assignments must be "sequence-specific", i.e., each resonance must be assigned to a spin in a particular amino acid residue in the protein sequence. NMR spectroscopy provides three types of information useful for spectral assignments: through-bond interactions (via scalar couplings), through-space interactions (via dipolar coupling), and chemical environment (via the chemical shift). The strategies employed for resonance assignments depend on the size of the protein under investigation and whether only homonuclear $^1$H NMR spectra are available (unlabeled proteins) or whether $^{13}$C and $^{15}$N heteronuclear correlation spectra are available (isotopically labeled proteins).

Conventional homonuclear multi-dimensional NMR techniques can be employed using unlabeled proteins to determine structures of proteins up to about 100 residues [e.g., Wüthrich, in *NMR of Proteins and Nucleic Acids*, Wiley, New York (1986); Wüthrich, *Science*, 243: 45-50 (1989); Clore and Gronenbom, *Ann Rev Biophys Chem*, 21: 29-63 (1991)] which are comparable in quality to 2-2.5 Å resolution X-ray structures [Clore and Gronenbom, *J Mol Biol*, 221: 47-53 (1991)]. However, for proteins larger than about 100 residues, such as helicase fragments of the present invention, conventional homonuclear assignment strategies can no longer be applied successfully and multi-dimensional heteronuclear NMR experiments must be employed using isotopically labeled proteins [e.g., Clore and Gronenbom, in *NMR of Proteins*, Clore and Gronenbom, eds., CRC Press, Boca Raton, pp 1-32 (1993)]. For the present invention a combination of standard double- and triple-resonance experiments to achieve NMR resonance assignments of isotopically labeled HCV NS3 helicase fragments [e.g., Markley and Kainosho, in *NMR of Macromolecules: A Practical Approach*, Roberts, ed., IRL Press, Oxford, pp 101-152 (1993); Cavanagh et al., in *Protein NMR Spectroscopy: Principles and Practice*, Academic Press, San Diego, pp 410-556 (1996)] can be used.

Details of the local backbone geometry can be obtained by an extension of the sequential assignment process; the relative intensities of $d_{NN}$ (NOE between amide protons), $d_{\alpha N}$ (NOE between alpha proton and amide proton), and $d_{\beta N}$ (beta proton and amide proton) NOE cross-peaks and the measurement of the backbone $^3J_{HNH\alpha}$ (intra-residue three-bond coupling constant between amide proton and alpha proton) are required. The combination of sequential NOE and $^3J_{HNH\alpha}$ coupling constant data together with medium range and a few long range NOEs is capable of providing details of the regions of regular secondary structure within the protein. Evidence of regular secondary structures can be corroborated by analysis of the amide exchange rates. The elements of secondary structures can be connected together to give a crude view of the global fold by the identification of a few key long-range NOEs. Thus, without recourse to extensive calculations and data analysis, important structural details (albeit of low absolute resolution) can be obtained in a straightforward manner [e.g., Barsukov and Lian, in *NMR of Macromolecules: A Practical Approach*, Roberts, ed., IRL Press, Oxford, pp 315-357 (1993)].

In addition to the NOE, coupling constant, and amide exchange data, it has been well established in recent years to use information that is contained in the chemical shift data of the protein to derive its secondary structure. The nuclear chemical shift is very sensitive to its local electronic environment. Since the chemical shifts of the protein, especially those of $^1H^\alpha$, $^{13}C^\alpha$, $^{13}C^\beta$, and $^{13}C'$ nuclei, are correlated with its secondary structure, they can provide important information regarding the secondary structure of the protein [e.g., Spera and Bax, *J Am Chem Soc*, 113: 5490-5492 (1991); Wishart et al., *Biochemistry*, 31: 1647-1651 (1992); Wishart and Sykes, *Methods in Enzymology*, 239: 363-392 (1994); Cornilescu et al., *J Biomol NMR*, 13: 289-302 (1999)]. Among various empirical approaches to extract structural information from chemical shift data, the chemical shift index method has been widely accepted in the NMR community. In this approach a chemical shift index (CSI) is assigned to each residue of the protein based on a comparison between the chemical shifts of the $^1H^\alpha$, $^{13}C^\alpha$, $^{13}C^\beta$, $^{13}C'$ nuclei which are determined on the folded protein with those corresponding to random coil chemical shifts. The secondary structure elements can then be identified by examination of these chemical shift indices according to established rules [Wishart and Sykes, *Methods in Enzymology*, 239: 363-392 (1994)]. Thus, NOE, coupling constant, amide exchange data, and CSI data can be used to confirm the secondary structure elements and the global folds of HCV NS3 helicase fragments and full length protein.

The fragments of the invention are ideal for use in NMR-based drug discovery techniques to discover, optimize, and synthesize chemical entities, including inhibitory compounds that are capable of binding to HCV NS3 helicase fragments or any protein thereof. Assignments of the amide resonances of the target protein are an important step in these processes. This will allow determination of the location of the ligand-binding site(s) by analyzing the specific amide signals of the protein that change upon the addition of the compound. Thus, "hits" can immediately be judged inadequate if they are observed to disrupt the protein fold or bind to an undesired location. Having various subdomain HCV NS3 helicase constructs, it is possible to obtain resonance assignments for the smaller constructs first and then correlate them with the larger multi-domain constructs. This approach greatly simplifies and accelerates the assignment process of the larger multi-domain HCV NS3 helicase constructs. This is particularly true for constructs derived from HCV NS3 helicase subdomains I and II (e.g., subdomain I,IIΔ derived from amino acids 181-430,SDGK,452-481 of HCV NS3) since the domain-domain interactions between domain I and II are very much localized and minimal. To obtain backbone assignments for proteins of molecular weight smaller than about 20 kDa is relatively easy and fast with current NMR methodologies. In contrast, this is still a challenge and a much slower process for larger polypeptides, such as fragments of HCV NS3 subdomain I,IIΔ (e.g., fragments derived from 181-430, SDGK,452-481 of HCV NS3).

Crystallization and X-ray Crystallographic Analysis

Another aspect of the invention relates to preparation of crystals of HCV NS3 helicase fragments. Preferably, an HCV NS3 helicase fragment is produced recombinantly in *E. coli* and initial purification is accomplished by nickel chelate chromatography, as described supra. This HCV NS3 helicase subdomain preparation may be subjected to anion exchange chromatography for further purification. It may also be desirable to subject the HCV NS3 helicase subdomain preparation to standard size exclusion gel filtration. The protein fragment preparation may be further concentrated using any desirable standard technique. Finally, the preparation can be ultracentrifugated to produce a monodisperse helicase fragment preparation. The resulting supernatant is useful for crystallization purposes.

To prepare the supernatant for crystallization, a stabilizing solution is added, which preferably contains a protein stabilizing agent, a salt, a buffering agent to adjust pH, and optionally a reducing agent or an oxygen scavenger is added. The protein stabilizing agent and salt maintain the solubility of the HCV NS3 helicase protein fragment preparation. Protein stabilizing agents, also known as cosmotropic agents, are well known in the art, and include polyols, sugars as well as amino acids and amino acid analogs, e.g., erythritol, sorbitol, glycerol, fructose, trehalose, proline, β-alanine, taurine and glycine betaine [see Jeruzalmi & Steitz, *J Mol Biol*, 274: 748-756 (1997)]. The concentration of a stabilizing agent will vary depending upon the type of agent employed. For example, glycerol is preferably provided in a concentration range from about 2 to about 20% (w/v), preferably about 10% (w/v). The salt may be provided in a concentration from about 0-2000 mM. Many salts are routinely used for this purpose. If desired, the reducing agent is present in the buffered solution at a concentration of about 10 mM. Examples of reducing agents include dithiothreitol (DTT) and dithioerythritol (DET), but it is preferably β-mercaptoethanol (BME). The final pH of the stablizing solution can range from 3.5 to 8, preferably between pH5 and 6.

A "precipitant" compound can be used to decrease the solubility of the polypeptide in a concentrated solution. Alternatively, a "precipitant" is a change in a physical or chemical parameter, including temperature, pH and salt concentrations, which decreases polypeptide solubility. Precipitants induce crystallization by forming an energetically unfavorable precipitant-depleted layer around the polypeptide molecules. To minimize the relative amount of this depletion layer, the polypeptides form associations and ultimately crystals [see Weber, *Advances in Protein Chemistry*, 41: 1-36 (1991)]. Various precipitants are known in the art including, e.g., ammonium sulfate, ethanol, 2-methyl-2,4-pentanediol, and polyglycols. A suitable precipitant for crystallization of NS3/NS4A polypeptide complex is polyethylene glycol (PEG), which combines some of the characteristics of the salts and other organic precipitants. In addition to precipitants, other materials can be added to the polypeptide crystallization solution, including buffers to adjust the pH of the solution (and hence surface charge on the peptide) and salts to reduce the solubility of the polypeptide.

Crystallization of NS3 helicase fragments of the invention can be accomplished using any of the various known methods in the art [see e.g., Giegé et al., *Acta Crystallogr*, D50: 339-350 (1994); McPherson, *Eur J Biochem*, 189: 1-23 (1990)]. Such techniques include microbatch, hanging drop, seeding and dialysis. Preferably, hanging-drop vapor diffusion [McPherson, *J Biol Chem*, 251: 6300-6303 (1976)] or microbatch methods [Chayen, *Structure*, 5: 1269-1274 (1997)] are used. In each of these methods, it is important to promote continued crystal growth after nucleation by maintaining a supersaturated solution. In the microbatch method, polypeptide is mixed with precipitants to achieve supersaturation, and the vessel is sealed and set aside until crystals appear. In the dialysis method, the polypeptide is retained in a sealed dialysis membrane which is placed into a solution containing precipitant. Equilibration across the membrane increases the precipitant concentration thereby causing the polypeptide to reach supersaturation levels.

The following crystallization method, which was used to crystallize HCV NS3 helicase subdomain I (aa 181-324), can be used to crystallize an HCV helicase fragment. Preferably, the protein fragment concentration is at least 1 mg/mL and less than 60 mg/mL. Crystallization is achieved in a precipitant solution, which contains a precipitant compound, e.g., 2-methyl-2,4-pentanediol, having a concentration from about 5 to 35% (w/v). A protein stabilizing agent, e.g., 0.5 to 20% glycerol, may also be included as desired. A suitable salt, e.g., sodium chloride, can also be added as desired, preferably in concentration ranging from 1 to 1000 mM. The pH of the precipitant is buffered to about 4.0 to 6.8, most preferably about pH 5 to 6. Specific buffers useful in a precipitant solution can vary and are well-known in the art e.g., MES, sodium cacodylate, sodium phosphate and sodium acetate [Scopes, *Protein Purification: Principles and Practice*, Third ed., Springer-Verlag, New York (1994)]. Crystals routinely grow in a wide range of temperatures, however it is preferred that crystals of the invention form at temperatures between about 1° C. and 26° C., preferably between about 2° C. and 12° C., and most preferably at about 4° C.

Crystals of the invention have a wide range of uses. For example, high quality crystals are suitable for X-ray or neutron diffraction analysis to determine the three dimensional structure of the corresponding subdomain of HCV NS3 helicase, and in particular to assist in the identification of active and effector sites for helicase. Knowledge of these sites and solvent accessible residues allow structure-based design and construction of agonists and antagonists for HCV NS3 helicase subdomain polypeptide complexes. In addition, crystallization can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing the high-quality crystals necessary for diffraction analysis. The crystallizable compositions of the invention can also be used for x-ray crystallography.

Once a crystal of the present invention is grown, X-ray diffraction data can be collected. One method for determining structure uses synchrotron radiation, under standard cryogenic condition for such X-ray diffraction data collection. Other methods for characterizing crystals of the invention include x-rays produced in a conventional source, e.g., a sealed tube or a rotating anode, precession photography, oscillation photography and diffractometer data collection.

The present invention permits the use of structure-based drug design techniques to design, select, and synthesize chemical entities, including inhibitory compounds that are capable of binding to HCV NS3 helicase subdomain polypeptide or any portion thereof. Also, de novo and iterative drug design methods can be used to develop drugs from the crystal structure of the present invention. One particularly useful drug design technique enabled by this invention is structure-based drug design, which optimizes associations between a protein and a compound by determining and evaluating the three-dimensional structures of successive sets of protein-compound complexes. HCV NS3 helicase fragment complexes suitable for crystallography analyses include, for example, a fragment of the invention in complex with a small-molecule, e.g., peptide, nucleotide, polynucleic acid (i.e. substrate), peptidomimetic nucleotide analog or an inhibitor unrelated in structure to substrate, members of the putative replicase complex (e.g., HCV NS5B, an RNA dependent RNA polymerase, NS2 or additional HCV proteins), one or more cellular host factors, and other molecules commonly used in such analyses, or combinations thereof.

The association of a natural ligand or substrate with the binding pocket of a corresponding receptor or enzyme is the basis of many biological mechanisms of action. The term "binding pocket", as used herein, refers to any region of a molecule or molecular complex that favorably associates with another chemical entity or compound as a result of its shape. Similarly, drugs may exert their biological effects through association with the binding pocket of a receptor or enzyme. Such association may occur with all or any part of the binding pockets. An understanding of such association for HCV helicase will help to design drugs having more favorable associations with the target helicase enzyme, and thus, improved biological effects. Therefore, this information is valuable in designing potential enzyme inhibitors against HCV NS3 helicase subdomain polypeptides complexes.

In iterative structure-based drug design, crystals of a series of protein/compound complexes are used to solve the three-dimensional structure of each complex. Such an approach can provide insight into the association between a helicase protein and inhibitor compound by selecting compounds with inhibitory activity, obtaining crystals of the complex, solving the three-dimensional structure of the complex, and comparing the associations between the complex and previously solved protein. By observing how changes in the compound affected the protein/compound associations, an inhibitor compound can be optimized.

Iterative structure-based drug design is carried out by forming successive protein-compound complexes followed by crystallizing each new complex, or by soaking (i.e., a process in which the crystal is transferred to a solution containing the compound of interest) a pre-formed protein crystal in the presence of a inhibitor, thereby forming a protein/compound complex and obviating the need to crystallize each individual protein/compound complex. It is an advantage that the HCV NS3 helicase fragment crystals of the invention can be soaked in the presence of one or more compounds, such as HCV NS3 helicase subdomain inhibitors, substrates or other ligands, to provide HCV NS3 helicase fragment polypeptide compound crystal complexes.

Structure coordinates of a helicase fragment can be used to determine the three-dimensional structure of HCV helicase, molecular complexes of HCV helicase, or molecules which contain a structurally similar feature to HCV NS3 helicase. Molecular replacement techniques can be used to obtain structural information about a crystallized molecule or molecular complex whose structure is unknown by obtaining an X-ray diffraction pattern from the crystallized molecule or molecular complex, and applying crystallographic phases derived from at least a portion of the structure coordinates derived from a helicase subdomain to the x-ray diffraction pattern to generate a three-dimensional electron density map of the molecule or molecular complex. In addition, the structure of an HCV NS3 helicase subdomain-compound complex can be determined from the structure coordinates of a fragment of the invention. For example, a helicase protein-compound complex can be crystallized and the structure elucidated using methods such as difference Fourier or molecular replacement.

All of the complexes referred to above can be studied using well-known X-ray diffraction techniques may be refined versus x-ray data to 3 Å resolution or better to an $R_{free}$ value of about 0.40 or less using computer software, e.g., X-PLOR [Yale University, 1992, distributed by Molecular Simulations, Inc.; see e.g., Blundell & Johnson, supra; *Meth, Enzymol.*, vol. 114 & 115, Wyckoff et al., eds., Academic Press (1985)]. This information can be used to optimize known HCV NS3 helicase inhibitors, and to design new HCV NS3 helicase inhibitors.

The following Examples are provided to further demonstrate aspects of the invention, and are not intended to limit the invention thereto.

EXAMPLES

Example 1

Construction, Expression and Purification of HCV NS3 Helicase Subdomain I pNS3$_{(181-324)}$ was derived from plasmid pJC84 [Grakoui et al., *J Virol*, 67: 1385-1395 (1993)] which encodes the entire NS3 region of the 1a strain of HCV (SEQ ID NO: 1). The gene encoding HCV NS3 helicase subdomain I (i.e., residues 181-324 of HCV NS3 helicase from HCV-1a) was PCR amplified from pJC84 using primers which incorporate a NdeI site at the 5' end of the gene and a HindIII site at the 3' end. The PCR product was digested with the appropriate enzymes, gel purified and ligated into pet28b(+) (Novagen, Madison, Wis.), which was also prepared with NdeI and HindIII. The ligation reaction was used to transform competent *E. coli* XL2-Blue (Stratagene, La Jolla, Calif.) which were selected on LB agar plates with kanamycin (30 µg/ml). Recombinant clones were identified by PCR gene amplification and sequencing. The resulting plasmid, pNS3$_{(181-324)}$, encodes a fusion protein of HCV NS3 helicase subdomain I (181-324) carboxy-terminal to a polyHis tag and thrombin cleavage site.

A single colony from *E. coli* BL21(DE3) transformed with pNS3$_{(181-324)}$ was used to initiate growth in LB broth supplemented with 30 µg/ml kanamycin. When the cell density reached an OD$_{600}$ of 1-2, the culture was used to inoculate M9 media [Lech and Brent, in *Current Protocols in Molecular Biology*, vol. 1, Ausubel et al. (eds), John Wiley and Sons, New York, (1998)] supplemented with 30 µg/ml kanamycin and 0.5 ml of 0.1 M thiamine. When the cell density reached an OD$_{600}$ of 0.7-1.0 the cell culture was cooled to 16° C. and recombinant protein expression was induced with IPTG (1 mM final concentration). Cells were harvested 16 hours after induction and stored at −20° C. until lysed.

The cell pellet was resuspended in 100 ml/L culture of lysis buffer containing BPER (Bacterial Protein Extraction Reagent; Pierce Chemical Company, IL), 300 mM NaCl, 0.2 mM DTT, 10% glycerol and 10 mM imidazole, pH 8.4, 5 ml/L protease inhibitor cocktail III (Pierce Chemical Company, IL) and 10,000 unit/L Benzonase. The suspension was homogenized using a glass homogenizer and incubated at room temperature for 20 minutes with gentle stirring. The lysate was cleared by centrifugation at 186,000×g for 20 minutes. The supernatant was added to 4 ml/L culture of Ni$^{2+}$ resin which had previously been equilibrated in lysis buffer without DTT. The lysate and resin mixture was incubated for 1 hour at 4° C. on a rotator. After 1 hour, the resin was pelleted by centrifugation and resuspended with 10 ml of pre-chilled wash buffer consisting of 20 mM Tris-HCl, 25 mM imidazole, 0.2 mM DTT, 500 mM NaCl, 0.1% BOG, and 10% glycerol, pH 8. The resin was pelleted by centrifugation and packed into a column. The resin was washed with additional wash buffer until the λ$_{max}$ 280 nm stabilized at a value close to zero. The bound recombinant protein was eluted with 250 mM imidazole, 1 mM DTT, 500 mM NaCl, and 10% glycerol, pH 8. 10 NIH units of thrombin were added per mg of fusion protein and the sample was dialyzed at 4° C. for 16 hours against 75 mM potassium phosphate, 1 mM DTT, 20% glycerol, pH 8. The sample was then dialyzed against gel filtration buffer (75 mM potassium phosphate, 5 mM DTT, 0.015% sodium azide, pH 8) for 4 hours. After dialysis the sample was concentrated to 3 ml and applied to a SUPERDEX (gel filtration material)-200 size exclusion column (26×60 cm, Amersham Pharmacia Biotech, NJ) equilibrated in gel filtration buffer containing 75 mM potassium phosphate, 5 mM DTT, pH 8. Fractions containing HCV NS3 helicase subdomain I (181-324), as judged by sodium dodecyl sulfate-polyacrylamide gel electrophoresis (SDS-PAGE), were pooled and concentrated for NMR to approximately 200 µM studies containing 75 mM potassium phosphate, 5 mM DTT, pH 8. This procedure yielded more than 16 mg of highly pure HCV NS3 helicase subdomain I (181-324) protein per liter of final *E. coli* growth culture. The protein was either stored at 4° C. if used within a week or at −20° C. for long term strorage.

Example 2

Construction, Expression and Purification of HCV NS3 Helicase Subdomain IIΔ

The helicase fragment of this example was prepared substantially as described in Example 1, except as otherwise noted.

pNS3$_{(327-430,SDGK,452-481)}$ was derived from plasmid pJC84. The gene encoding HCV NS3 helicase subdomain IIΔ (327-430,SDGK,452-481; SEQ ID NO: 4), i.e., residues 327-481 of helicase derived from HCV-1a with residues 431-451 replaced by the amino acid sequence SDGK (SEQ ID NO: 2), was constructed from pJC84 in two pieces. The DNA sequence encoding residues 327-430 was amplified with a NdeI site in the upstream primer and the nucleotides encoding S-D-G-K (SEQ ID NO: 2) in the reverse primer. The DNA sequence encoding residues 452-481 was amplified with the nucleotides encoding for S-D-G-K (SEQ ID NO: 2) in the forward primer and a HindIII site in the reverse primer. The amplified DNA fragments were purified and then mixed for another round of PCR using the same forward primer used to amplify the DNA encoding residues 327-430 and the same reverse primer used to amplify the DNA encoding residues 452-481. The resulting products were digested with NdeI and HindIII, purified, and ligated into pet28b(+). The ligation reaction was used to transform competent *E. coli* XL2-Blue which were selected on LB agar plates with kanamycin (30 µg/ml). Recombinant clones were identified as described. The resulting plasmid, pNS3$_{(327-430,SDGK,452-481)}$, encodes a fusion protein of HCV NS3 helicase subdomain IIΔ (327-430,SDGK,452-481) carboxy-terminal to a polyHis tag.

The pNS3$_{(327-430,SDGK,452-481)}$ was used to transform *E. Coli* BL21(DE3), which were grown as described above in Example 1. Protein expression was induced, cells were harvested 3 hours after induction and then stored at −20° C.

The cell pellet was resuspended in lysis buffer (pH 7.5) and homogenized. The lysate was cleared and the supernatant added to 1 ml of Ni$^{2+}$ resin as described. The lysate and resin mixture was incubated for 1 hour at 7° C. on a rotator. After 1 hour the resin was pelleted by centrifugation and resuspended with 10 ml of pre-chilled wash buffer (20 mM HEPES, pH 6.5, 25 mM imidazole. 0.2 mM DTT, 500 mM NaCl, and 10% glycerol). The resin was pelleted by centrifugation, and washed on a column with additional wash buffer. Protein was eluted with 250 mM imidazole, 20 mM HEPES, 1 mM DTT, 500 mM NaCl, and 10% glycerol, pH 6.5. 10 NIH units of thrombin were added per mg of fusion protein and the sample was dialyzed at 7° C. for 16 hours against 20 mM HEPES, pH 6.5, 1 mM DTT, and 10% glycerol. The sample was dialyzed against gel filtration buffer consisting of 75 mM potassium phosphate, 5 mM DTT, 0.015% sodium azide, pH 6.5 for 4 hours. After dialysis the sample was concentrated as described. Fractions containing HCV NS3 helicase subdomain IIΔ (327-430,SDGK,452-481) as judged by SDS-PAGE were pooled and concentrated as described above. This procedure yielded approximately 5 mg of highly pure HCV NS3 helicase subdomain IIΔ (327-430,SDGK,452-481) protein per liter of final *E. coli* growth culture. The protein was stored as described above.

Example 3

Construction, Expression and Purification of HCV NS3 Helicase subdomain I,IIΔ

The helicase fragment of this Example was prepared substantially as described in Example 1, except as otherwise noted.

pNS3$_{(181-430,sDGK,452-481)}$ was derived from plasmid pJC84. The gene encoding HCV NS3 helicase subdomain I,IIΔ (181-430,SDGK,452-481; SEQ ID NO: 5), i.e., residues 181-481 of helicase derived from HCV-1a with residues 431-451 replaced by amino acids SDGK (SEQ ID NO: 2), was constructed from pJC84 in two pieces. The DNA sequence encoding residues 181-430 was amplified with a NdeI site in the upstream primer and the nucleotides encoding the amino acid sequence SDGK (SEQ ID NO: 2) in the reverse primer. The DNA sequence encoding residues 452-481 was amplified with the nucleotides encoding S-D-G-K (SEQ ID NO: 2) in the forward primer and a HindIII site in the reverse primer. The amplified DNA fragments were subjected to another round of PCR using the forward primer for residues 181-430 and the reverse primer for residues 452-481. The products were digested with NdeI and HindIII, purified, and ligated into pet28b(+). The ligation reaction was used to transform competent *E. coli* XL2-Blue and recombinant clones were identified as described. The resulting plasmid, pNS3$_{(181-430,SDGK,452-481)}$, encodes a fusion protein of HCV NS3 helicase subdomain I,IIΔ (181-430,SDGK,452-481) carboxy-terminal to a polyHis tag.

The pNS3$_{(181-430,SDGK,452-481)}$ was used to transform *E. coli* BL21(DE3), which were grown as described. When cell density reached an OD$_{600}$ of 1.5, recombinant protein expression was induced, and cells were harvested after 3 hours and stored at −20° C.

The cell pellet was resuspended in lysis buffer (pH 8), and incubated at room temperature for 20 minutes with gentle stirring. The lysate was cleared and the supernatant added to 1 ml of Ni$^{2+}$ resin per 100 ml of lysate as described. The lysate and resin mixture was incubated for 1 hour at 7° C. on a rotator. After 1 hour, the resin was pelleted by centrifugation and resupended with 10× resin volume of pre-chilled wash buffer (1% n-octyl-β-D-glucopyranoside, 50 mM potassium phosphate, 50 mM imidazole. 0.2 mM DTT, 300 mM NaCl, and 10% glycerol, pH 8). The resin was pelleted and washed on a column with additional wash buffer. Protein was eluted with 1% n-octyl-β-D-glucopyranoside, 250 mM imidazole, 1 mM DTT, 300 mM NaCl, and 20% glycerol, pH 7. 10 NIH units of thrombin were added per mg of fusion protein and the sample was dialyzed at 7° C. for 16 hours against 50 mM potassium phosphate, 1 mM DTT, 300 mM NaCl, and 20% glycerol, pH 7. The sample was dialyzed against gel filtration buffer consisting of 75 mM potassium phosphate, 50 mM NaCl, 5 mM DTT, 0.015% sodium azide, pH 6.5 for 4 hours. After dialysis the sample was concentrated as described. Fractions containing HCV NS3 helicase subdomain I,IIΔ (181-430,SDGK,452-481) as judged by SDS-PAGE were pooled and concentrated as described. This procedure yielded approximately 9 mg of highly pure HCV NS3 helicase subdomain I,IIΔ (181-430,SDGK,452-481) protein per liter of final *E. coli* growth culture. The protein was stored as described.

Example 4

Construction, Expression, and Purification of HCV NS3 Helicase Subdomain I,IIIΔ

The helicase fragment of this Example was prepared substantially as described in Example 1, except as otherwise noted.

pNS3$_{(181-327,483-572)}$ was derived from plasmid pJC84. The gene encoding HCV NS3 helicase subdomain I,IIIΔ (181-327, 483-572; SEQ ID NO: 6), i.e., residues 181-572 of helicase from HCV-1a with residues 328-482 deleted, was constructed from pJC84 in two pieces. The DNA sequence encoding residues 181-327 was amplified with a NdeI site in the upstream primer. The DNA sequence encoding for residues 483-572 was amplified with the nucleotides encoding a HindIII site in the reverse primer. The amplified DNA fragments were purified and subjected to another round of PCR using the same forward and reverse primers. The products were digested with NdeI and HindIII, purified, and ligated into pET28b(+). *E. coli* DH5α were transformed with the plasmid, and selected on LB agar plates with kanamycin (30 μg/ml). Recombinant clones identified as described. The resulting plasmid, pNS3$_{(181-327,483-572)}$, encodes a fusion protein of HCV NS3 helicase subdomain I,IIIΔ (181-327, 483-572) carboxy-terminal to a polyHis tag.

The pNS3$_{(181-327,483-572)}$ was used to transform *E. coli* BL21 (DE3), which were grown as described. At OD$_{600}$ 1-2 the culture was used to inoculate an M9 culture for expression. When the cell density reached OD$_{600}$ 0.7-1.0, the temperature was adjusted to 16° C., and protein expression was induced. Cells were harvested 16 hours after induction and frozen at minus 20° C. prior to purification.

The cell pellet was resuspended in lysis buffer (pH 8.4) and homogenized. The lysate was cleared and the supernatant was added to 4 ml/L culture of Ni$^{2+}$ resin as described. The lysate and resin mixture was incubated for 1 hour at 4° C. on a rotator. After 1 hour, the resin was pelleted and resuspended in 10 ml of pre-chilled wash buffer (20 mM Tris-HCl, 25 mM imidazole, 0.2 mM DTT, 500 mM NaCl, 0.1% BOG and 10% glycerol, pH 8). The resin was pelleted, washed on a column with additional wash. Protein was eluted with 250 mM imidazole, 1 mM DTT, 500 mM NaCl, and 10% glycerol, pH 8. Ten NIH units thrombin were added per mg of fusion protein and the sample was dialyzed at 4° C. for 16 hours against 75 mM potassium phosphate, 1 mM DTT, pH 8. After dialysis the sample was concentrated to approximately 15 mg/ml and applied to a SUPERDEX (gel filtration material)-200 size exclusion column (26×60 cm, Amersham Pharmacia Biotech, NJ) equilibrated in gel filtration buffer containing 75 mM potassium phosphate, 5 mM DTT, pH 8. Fractions containing HCV NS3 helicase subdomain I,IIIΔ (181-327, 483-572) as judged by SDS-PAGE were pooled and concentrated as described. This procedure yielded approximately 1-2 mg of highly pure HCV NS3 helicase subdomain I,IIIΔ (181-327, 483-572) protein per liter of final *E. coli* growth culture. The protein was stored as described.

Example 5

Construction, Expression and Purification of HCV NS3 Helicase Subdomain I Mutant The helicase fragment of this example was prepared substantially as described in Example 1, except as otherwise noted.

pNS3$_{(181-324,R257E)}$ was derived from plasmid pNS3$_{(181-324)}$ with an Arg-to-Glu point mutation at position 257, i.e., amino acid residues 181-324 of HCV NS3 helicase from HCV-1a (SEQ ID NO: 3) contained a single mutation at Arg-257, which was replaced by a glutamic acid. The plasmid pNS3$_{(181-324,R257E)}$ was generated by a QUIKCHANGE (site-directed mutagenesis kit) PCR reaction (Stratagene, Cloning Systems, La Jolla, Calif.) using primers having the sequence ATCAGGACCGGGGTGGAAACAATTAC-CACTGGC (SEQ ID NO: 15) and GCCAGTGGTAAT-TGTTTCCACCCCGGTCCTGAT (SEQ ID NO: 16). The reaction mixture was used to transform competent *E. coli* XL2-Blue, which were selected on LB agar plates with kanamycin (30 μg/ml). Recombinant clones were identified as described. The resulting plasmid, pNS3$_{(181-324,R257E)}$, encodes a fusion protein of HCV NS3 helicase subdomain I (181-324) carboxy-terminal to a polyHis tag and thrombin cleavage site, having a mutation at amino acid residue 257 (Arg) to a Glu.

The pNS3$_{(181-324,P257E)}$ was used to transform *E. coli* BL21(DE3), which were grown as described above in Example 1. Protein expression and purification are essentially the same as described in Example 1.

Example 6

Oligomerization States of HCV NS3 Helicase Subdomain I and Subdomain I Mutant The oligomerization states of helicase fragments corresponding to HCV NS3 helicase subdomain I (181-324) and subdomain I (181-324,R257E) mutant were determined using size exclusion chromatography.

The molecular weight determinations of HCV NS3 helicase subdomain I and the subdomain I (181-324,R257E) mutant were performed in 75 mM KPO4, pH 7.6, 5 mM DTT, 0.015% NaN3 using a SUPERDEX (gel filtration material)-75 gel filtration column (Amersham Pharmacia Biotech, Piscataway, N.J.) at 4° C. Protein absorbance was monitored at 280 nm. Molecular weight standards, Aprotinin (6.5 kDa), Cytochrome c (12.4 kDa), Carbonic anhydrase (29 kDa), Bovine serum albumin (66 kDa), and Blue dextran (2,000 kDa) (Sigma Chemical Co. Saint Louis, Mo.) were used to construct a plot of log (molecular weight) versus elution volume [e.g., Boyer, in *Modern Experimental Biochemistry*, Benjamin/Cummings, California, (1993)]. The concentrations of the protein samples (50 μl) used in these experiments were: 1.0, 1.6, 3.2, 10.0 mg/ml for HCV NS3 helicase subdomain 1 and 0.4, 2.0, 6.0 mg/ml for subdomain I (181-324, R257E) mutant.

The elution volume for subdomain I (181-324) decreased from 14.7 ml to 13.7 ml as the protein concentration was increased from 1.0 mg/ml to 10 mg/ml, corresponding to an apparent molecular weight increase from 17 to 22 kDa. This suggests that subdomain I (181-324) undergoes oligomerization with increasing concentration, i.e. subdomain I does not remain monomeric at higher concentrations, such as those tested. The elution volume of the subdomain I (181-324, R257E) mutant remained constant (at 14.5 ml) in increasing concentrations of protein (from 0.4 mg/ml to 6 mg/ml). These results indicate that the subdomain I (181-324,R257E) mutant remains monomeric at high protein concentrations, and therefore the R257E mutation can improve the solubility of HCV NS3 helicase subdomain I (181-324).

Example 7

Comparision of ATPase Activities of HCV NS3 Helicase and Subdomain I,IIΔ

The $K_m$ values for ATP and the apparent steady state affinities for single stranded RNA of HCV NS3 helicase and HCV NS3 helicase subdomain I,IIΔ (181-430,SDGK,452-481) in which residues 431-451 are replaced with S-D-G-K (SEQ ID NO: 2) were compared using a coupled spectrophotometric assay as previously described.

To determine the $K_m$ for ATP, helicase construct (40 nM) was assayed at 25° C. in 0.103 M sodium Mops buffer, pH 7.2, 2.6 mM MgCl$_2$, 0.28 mg/ml BSA, 0.4 mM DTT, 0.1 mM EDTA, 1 mM Tris-Cl, 1 mM sodium Hepes, 2 mM PEP, 20 U/ml LDH, 10 U/ml PK, 0.17 mM NADH, +525 μM polyU ([U]), plus 0.05, 0.1, 0.2, 0.4, 0.8 1.6 or 3.2 mM Mg-ATP.

To determine the constructs' relative steady state affinities for RNA, 20 nM of each was assayed as described above for $K_m$, with the following modifications: [Mg-ATP] was 10 mM; [MgCl$_2$] was 5.1 mM; and [U] was between 0 and 660 μM. Table 1 summarizes the ATPase activity parameters and results.

TABLE 1

| NS3 Helicase Construct | HCV NS3 helicase 181-631 | HCV NS3 helicase subdomain I, IIΔ |
|---|---|---|
| NA$^a$ Independent $k_{cat}$ | 1.6 sec$^{-1}$ | 5.5 sec$^{-1}$ |
| NA$^a$ Independent $K_{m-ATP}$ | 0.005 mM$^b$ | 2.1 mM |
| NA$^a$ Stimulated $k_{cat}$ | 36.7 sec$^{-1}$ | 23.6 sec$^{-1}$ |
| NA$^a$ Stimulated $K_{m-ATP}$ | 0.22 mM | 2.7 mM |
| Fold Stimulation by NA$^a$ | 23 | 4.3 |
| $K_{polyU}^c$ | 113 μM U | 260 μM U |

$^a$PolyU.
$^b$Preugschat et al., J Biol Chem 271: 24449-24457 (1996).
$^c$Concentration of polyU ([U]) resulting in 50% maximal stimulation.

Example 8

NMR Sample Preparation, NMR Spectrum of HCV NS3 Helicase Subdomain I

For NMR studies, HCV NS3 helicase subdomain I was adjusted to 100 to 150 μM with the addition of 10% D$_2$O, and 0.4 mM AEBSF [4-(2-Aminoethyl)-benzenesulfonyl fluoride, which is an irreversible serine protease inhibitor with high water solubility] (SIGMA, St. Louis, Mo.). The final buffer of the NMR sample contained 75 mM KPO$_4$, pH 8.0, 5 mM DTT, 10% D$_2$O, and 0.4 mM AEBSF. Two-dimensional (2D) $^{15}$N-HSQC NMR spectra were obtained on a 600 MHz Varian NMR spectrometer at 25° C. Sweep widths of 8000 Hz for $^1$H, centered on the water resonance, and 1824 Hz for $^{15}$N, centered at 119 ppm, were used. The data were collected with 16 scans with 64 or 128 t1 increment points in the 15N dimension. HCV NS3 helicase subdomain I was already aggregated at a concentration of 500 μM, as clearly indicated by the increased peak linewidths in an $^{15}$N-HSQC NMR spectrum. In contrast, the peak line widths at 150 μM were typical for a monomeric protein of this size. The number of peaks and their dispersion in the 2D $^{15}$N-HSQC NMR spectrum were indicative of a fully folded protein.

Example 9

NMR Sample Preparation and Spectrum of HCV NS3 Helicase Subdomain IIΔ

For NMR, studies HCV NS3 helicase subdomain IIΔ (327-430,SDGK,452-481), in which residues 431-451 are replaced with S-D-G-K (SEQ ID NO: 2), was adjusted to 100 to 250 µM as described in Example 8. The final buffer of the NMR sample contained 75 mM KPO$_4$, pH 6.5, 5 mM DTT, 10% D$_2$O and 0.4 mM AEBSF. An HSQC spectrum was obtained as described. The number of peaks and dispersion in a 2D $^{15}$N-HSQC NMR spectrum of HCV NS3 helicase subdomain IIΔ were indicative of a fully folded protein. In addition, the line widths of the peaks in the NMR spectrum were consistent with a monomeric protein with a molecular weight of 15 kDa.

Example 10

NMR Sample Preparation and Spectrum of HCV NS3 Helicase Subdomain I,IIΔ

After isolating HCV NS3 helicase subdomain I,IIΔ (181-430,SDGK,452-481) in which residues 431-451 are replaced with SDGK (SEQ ID NO: 2; described in Example 3), the protein was concentrated in a centrifugal filtration device to approximately 220 µM. Deuterium oxide was added to a final volume of 10%. The final sample was approximately 200 µM HCV NS3 helicase subdomain I,IIΔ, 75 mM KPO$_4$, 50 mM NaCl, 5 mM DTT, 0.015% sodium azide, pH 6.5. The sample was placed in a 500 MHz NMR spectrometer and equilibrated at 25° C. Data were collected with 32 scans for each of the 120 points in the indirect dimension and an HSQC spectrum was obtained. Sweep widths of 8000 Hz for $^1$H, centered on the water resonance, and 1833 Hz for $^{15}$N, centered at 119 ppm, were used. The number of peaks and dispersion in a 2D $^{15}$N-HSQC NMR spectrum of HCV NS3 helicase subdomain I,IIΔ were indicative of a fully folded protein. In addition, the line widths of the peaks in the NMR spectrum were consistent with a monomeric protein with a molecular weight of 30 kDa.

Example 11

NMR Sample Preparation and NMR Spectrum of HCV NS3 Helicase Subdomain I,IIIΔ

For NMR studies, HCV NS3 helicase subdomain I,IIIΔ (181-327, 483-572) in which residues 328-482 are deleted, was adjusted to approximately 100 µM, as described in Example 8. The final buffer was the same as Example 9. An HSQC spectrum was obtained as described. The number of peaks and dispersion in a 2D $^{15}$N-HSQC NMR spectrum of HCV NS3 helicase subdomain I,IIIΔ were indicative of a fully folded protein. In addition, the line widths of the peaks in the NMR spectrum were consistent with a monomeric protein with a molecular weight of 24 kDa.

Example 12

ATP Binding to HCV NS3 helicase subdomain I,IIΔ

NMR titration experiments were performed to determine if HCV NS3 helicase subdomain I,IIΔ (181-430,SDGK,452-481) retained ATP binding affinity. The dissociation constant ($K_d$) of ATP was derived from an analysis of the changes in amide chemical shifts of residues in the binding site of the protein as a function of ATP concentration. ATP (0.0002, 0.001, 0.005, 0.025, 0.05 M) was added incrementally to 200 µM [$^{15}$N]-labeled HCV NS3 helicase subdomain I,IIΔ in 75 mM potassium phosphate, 50 mM NaCl, 5 mM DTT, 0.015% sodium azide, pH 6.5. Two-D $^{15}$N-HSQC spectra of HCV NS3 helicase subdomain I,IIΔ (181-430,SDGK,452-481) were collected after each addition of ATP. A binding affinity of 7.68±0.03 mM was determined using data obtained from analyzing chemical shift perturbation data as a function of ATP concentration. The data supports the binding of a nucleotide as expected for a protein with NTPase activity.

The following describes the analytical method used to calculate ATP binding. The dissociation constant of ATP was derived from the amide chemical shift changes of protein residues at the binding site as a function of the concentration of ATP. For an interaction of a compound C with a protein R:

$$C + R \rightleftharpoons CR$$

$$K_d = \frac{k_{off}}{k_{on}} = \frac{[C][R]}{[CR]}$$

This equation can directly be correlated to chemical shifts as follows:

$$\frac{|\delta - \delta_f|}{|\delta_f - \delta_b|} = \frac{([C]_0 + [R]_0 + K_d) - \sqrt{([C]_0 + [R]_0 + K_d)^2 - 4[C]_0[R]_0}}{2[R]_0} \quad (1)$$

where $[C]_0$ and $[R]_0$ are the total concentrations of compound and protein, respectively, and $[CR]$ is the concentration of the complex, $\delta$ is the chemical shift of the protein measured at each concentration $[CR]$, $\delta_f$ is the chemical shift of the protein in the absence of the compound $[C]_0$=0, and $\delta_b$ is the chemical shift of the protein at saturation with compound.

Nonlinear regression methods were used to estimate $K_d$ and $\delta_b$ in the titration experiment. Data from an experiment consist of chemical shift ($\delta$) values measured at a number of different compound concentrations. The values of $[C]_0$, $[R]_0$, and $\delta_f$ are known. Estimates of $K_d$ and $\delta_b$ are computed by fitting the data to Equation (1), supra using nonlinear least squares in the statistical package SAS (Institute Inc, Cary, N.C.). From a nonlinear fit, estimates of the standard errors were obtained for $K_d$ and $\delta_b$

Example 13

Backbone NMR Resonance Assignments and Secondary Structure of HCV NS3 Helicase Subdomain IIΔ (327-430,SDGK,452-481)

[$^{15}$N]- and [$^{15}$N/$^{13}$C]-labeled NMR samples of HCV NS3 helicase subdomain IIΔ (327-430,SDGK,452-481; SEQ ID NO: 4) in which residues 431-451 are replaced with SDGK (SEQ ID NO: 2) were prepared to obtain sequential resonance assignments. The protein concentration was about 0.6 mM in a buffer system containing 75 mM KPO$_4$, pH 6.5, 5 mM DTT, 5% D$_2$O, 0.4 mM AEBSF, and 0.015% NaN$_3$. $^{15}$N-HSQC, 3D $^{15}$N-edited NOESY-HSQC and $^{15}$N-edited TOCSY-HSQC NMR spectra were acquired using a uniformly [$^{15}$N]-labeled sample. 3D triple resonance experiments, such as HNCO, HNCACB, CBCA(CO)NH, and (H)C(CO)NH-(TOCSY) were acquired using a uniformly [$^{15}$N/$^{13}$C]-labeled sample. The sample for the hydrogen-deuterium exchange experiments was prepared by dissolving a lypholized protein sample into 99.99% D$_2$O at a concentration of 0.5 mM in 75 mM K$_i$PO$_4$, pH 6.5, 5 mM DTT, 0.4 mM AEBSF and 0.015% NaN$_3$. The protein sample was immediately placed in the NMR spectrometer, and a series $^{15}$N-$^1$H HSQC spectra were collected over time. All NMR experiments were performed on a Varian INOVA 500 MHz spectrometer at 25° C. NMR data were processed using FELIX98 (MSI, San Diego) and analyzed using NMRView on a SGI workstation.

Sequential assignments of $^1H^N$, $^{15}N$, $^{13}C^\alpha$ and $^{13}C^\beta$ were derived from the 3D HNCACB and CBCA(CO)NH NMR triple-resonance experiments by analyzing the sequential connectivities of $^{13}C^\alpha$ and $^{13}C^\beta$ chemical shifts. $^{13}C'$ chemical shifts were obtained from a 3D HNCO NMR experiment. $^3J_{HNH\alpha}$ coupling constants were obtained from analysis of a 3D HNHA data set.

131 of the expected 132 non-proline backbone amide $^{15}N/^1H^N$ NMR resonances have been sequence-specifically assigned (see Table 2, infra). In addition, backbone $^{13}C'$, $^{13}C'^\alpha$ and $^{13}C^\beta$ (for non-glycine residues) NMR resonances have been assigned. $^3J_{HNH\alpha}$ coupling constants were obtained for 80 out of the 132 non-proline residues. 51 amide proton signals were detected during the hydrogen-deuterium exchange experiments. Preliminary analysis of $^{15}N$-edited NOE spectra indicates that the overall fold of this isolated domain is similar to the corresponding part in the crystal structure of full-length HCV NS3 helicase.

Figure 3:
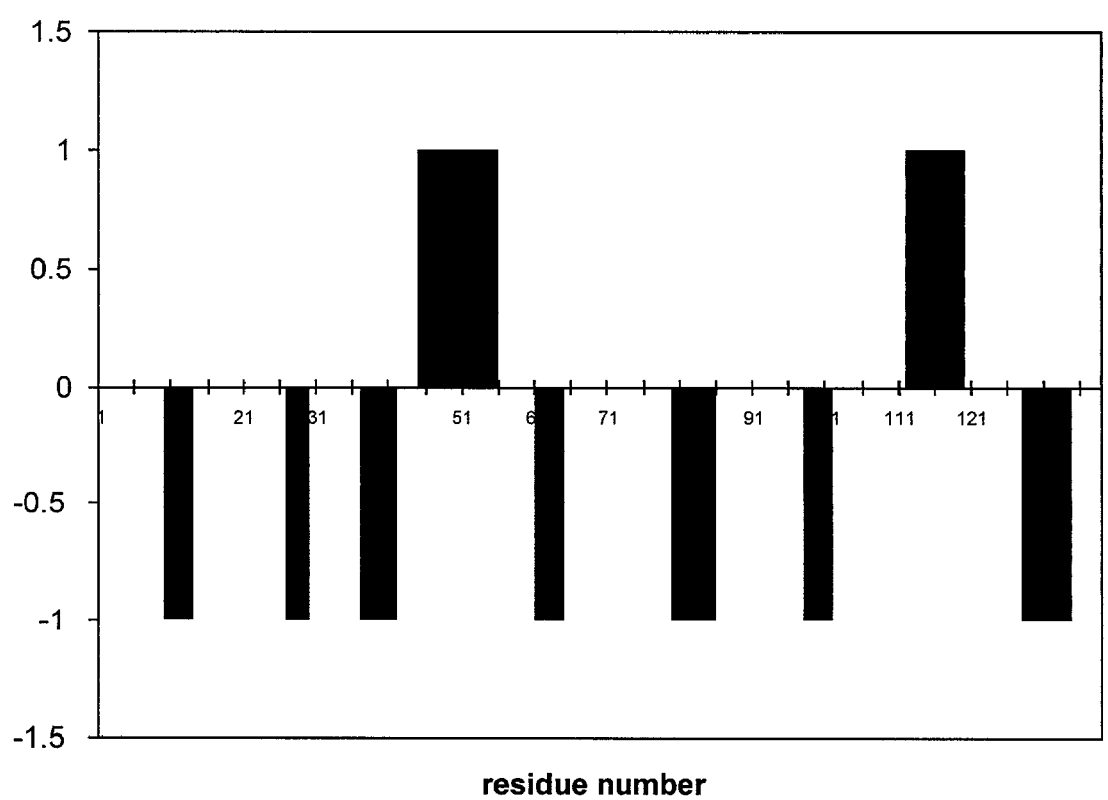
FIG. 3 depicts a chemical shift index (CSI) for an engineered HCV NS3 helicase subdomain II construct (SEQ ID NO: 4).

The chemical shift index (CSI) method was used to predict the secondary structure of HCV NS3 helicase subdomain IIΔ (327-430,SDGK,452-481) in which residues 431-451 are replaced with S-D-G-K (SEQ ID NO: 2). The chemical shift index was calculated using the CSI program (Wishart and Sykes, 1994, software provided by Wishart) using $^1H^\alpha$, $^{13}C'$, $^{13}C'^\alpha$, and $^{13}C^\beta$ chemical shifts to determine well-defined regions of β-sheet and α-helical secondary structure (FIG. 3). The CSI indicates that residues 336-339, 353-359, 363-367, 387-391, 406-411, 424-427, and 471-477 are in the β-sheet conformation, whereas residues 371-381 and 455-462 are in a α-helical conformation of SEQ ID NO: 1. This secondary structure prediction is in very good agreement with the secondary structure elements that are observed for the corresponding part in the crystal structure of full-length HCV NS3 helicase [Yao et al., *Nat Struct Biol*, 4: 463-467 (1997)]. Although there are some differences between the starting and ending residues in the secondary structure elements predicted by the CSI when compared to those of the crystal structure, all differences are within the accuracy of the CSI method. There are however two regions of secondary structure that are not predicted by the CSI; in the crystal structure of full-length HCV NS3 helicase residues 347-349 and 356-359 of SEQ ID NO: 1 are in a β-sheet and α-helical conformation, respectively. Nevertheless, NOE, coupling constant, and amide exchange data for these residues are consistent with the secondary structure of the crystal structure. Strong $d_{\alpha N(i,i+1)}$ NOEs were observed for residues 347-349 with large $^3J_{HNH\alpha}$ coupling constants (7.6 Hz and 7.5 Hz for residue 347 and 349, respectively) which is consistent with residues 347-349 adopting a β-sheet conformation. Strong $d_{NN(i,i+1)}$ NOEs were observed for residues 356-359, and residue 356 showed $d_{\alpha N(i,i+2)}$ and $d_{\alpha N(i,i+3)}$ NOEs. In addition, small $^3J_{HNH\alpha}$ coupling constants of 2.2 Hz and 2.1 Hz were detected for residues 356 and 357, respectively. Moreover, the hydrogen-deuterium exchange experiments revealed that residue 359 is highly protected from the solvent solution suggesting that its amide proton is hydrogen bonded. These data suggest that residues 356-359 form a β-turn conformation like in the crystal structure.

The following Table 2 contains the backbone NMR resonance assignments of HCV NS3 helicase subdomain IIΔ (327-430,SDGK,452-481; SEQ ID NO: 4) in which residues 431-451 are replaced with amino acids SDGK (SEQ ID NO: 2). The table contains one line for each residue. From left to right, the columns indicate residue number, 3-letter amino acid code, chemical shift of $^1H^N$, chemical shift of $^{15}N$, chemical shift of $^{13}C^\alpha$, chemical shift of $^{13}C^\beta$, and chemical shift of $^{13}C'$ (n.a., not available; n.d., not determined).

TABLE 2

| resi_num | AA | HN | 15N | CA | CB | C' |
|---|---|---|---|---|---|---|
| 327 | GLY | 8.42 | 111.17 | 45.12 | n.a. | 173.42 |
| 328 | SER | 8.21 | 116.62 | 57.75 | 63.30 | 172.89 |
| 329 | VAL | 8.17 | 122.36 | 61.66 | 32.35 | 171.20 |
| 330 | THR | 8.23 | 119.53 | 61.30 | 68.60 | 173.36 |
| 331 | VAL | 8.19 | 125.27 | 59.07 | 32.11 | n.d. |
| 332 | PRO | n.a | n.d. | 62.91 | 31.69 | 171.25 |
| 333 | HIS | 8.62 | 121.70 | 52.78 | 29.53 | n.d. |
| 334 | PRO | n.a | n.d. | 62.91 | 31.58 | 170.91 |
| 335 | ASN | 9.01 | 120.94 | 52.84 | 39.01 | 173.36 |
| 336 | ILE | 7.80 | 120.24 | 59.89 | 41.06 | 172.30 |
| 337 | GLU | 8.17 | 129.72 | 54.71 | 30.94 | 172.61 |
| 338 | GLU | 8.91 | 127.02 | 54.71 | 30.11 | 170.81 |
| 339 | VAL | 9.41 | 126.64 | 60.01 | 34.82 | 173.64 |
| 340 | ALA | 8.46 | 132.53 | 51.18 | 18.22 | 167.88 |
| 341 | LEU | 8.22 | 123.16 | 54.84 | 42.71 | 170.58 |
| 342 | SER | 9.08 | 120.52 | 55.19 | 64.96 | 173.82 |
| 343 | THR | 8.01 | 106.69 | 61.66 | 67.56 | 173.00 |
| 344 | THR | 8.12 | 119.72 | 61.54 | 67.60 | 174.77 |
| 345 | GLY | 7.99 | 113.72 | 43.41 | n.a. | 175.15 |
| 346 | GLU | 8.96 | 121.04 | 59.66 | 29.88 | 170.68 |
| 347 | ILE | 7.70 | 118.97 | 56.13 | 38.24 | n.d. |
| 348 | PRO | n.a. | n.d. | 62.91 | 31.69 | 170.56 |
| 349 | PHE | 8.49 | 125.67 | 58.24 | 41.05 | 174.54 |
| 350 | TYR | 8.36 | 124.32 | 59.60 | 35.56 | 172.48 |
| 351 | GLY | 8.21 | 105.55 | 44.71 | n.a. | 173.05 |
| 352 | LYS | 8.01 | 122.25 | 52.13 | 32.11 | 172.38 |
| 353 | ALA | 8.47 | 125.53 | 51.07 | 21.05 | 172.56 |
| 354 | ILE | 9.09 | 121.24 | 57.18 | 41.30 | n.d. |
| 355 | PRO | n.a. | n.d. | 60.25 | 31.41 | 170.01 |
| 356 | LEU | 9.19 | 128.23 | 56.83 | 41.41 | 168.70 |
| 357 | GLU | 8.77 | 113.91 | 58.60 | 28.94 | 169.09 |
| 358 | VAL | 7.03 | 108.58 | 61.31 | 30.23 | 170.92 |
| 359 | ILE | 7.11 | 111.96 | 59.54 | 38.47 | 173.72 |
| 360 | LYS | 6.93 | 122.62 | 57.07 | 31.76 | 171.79 |
| 361 | GLY | 7.78 | 114.24 | 43.89 | n.a. | 173.54 |
| 362 | GLY | 8.24 | 112.47 | 43.86 | n.a. | 174.44 |
| 363 | ARG | 8.59 | 121.41 | 54.24 | 31.29 | 172.43 |
| 364 | HIS | 8.90 | 124.02 | 54.36 | 35.05 | 175.62 |
| 365 | LEU | 8.05 | 126.86 | 52.24 | 43.30 | 174.33 |
| 366 | ILE | 9.35 | 126.92 | 59.07 | 40.12 | 172.53 |
| 367 | PHE | 9.12 | 124.65 | 56.95 | 41.78 | 170.60 |
| 368 | CYS | 8.75 | 116.86 | 56.95 | 31.53 | 171.66 |
| 369 | HIS | 8.45 | 117.76 | 56.95 | 31.29 | 173.69 |
| 370 | SER | 6.81 | 112.85 | 54.28 | 66.92 | 173.81 |
| 371 | LYS | 8.78 | 124.90 | 59.14 | 31.04 | 170.56 |
| 372 | LYS | 7.87 | 119.20 | 58.72 | 31.88 | 168.19 |
| 373 | LYS | 7.53 | 119.19 | 56.72 | 30.82 | 168.71 |
| 374 | CYS | 7.68 | 118.42 | 62.48 | 26.46 | 173.02 |
| 375 | ASP | 8.13 | 119.72 | 56.95 | 39.64 | 167.86 |
| 376 | GLU | 8.13 | 121.70 | 58.60 | 29.88 | 168.06 |
| 377 | LEU | 8.76 | 122.22 | 57.30 | 40.83 | 168.57 |
| 378 | ALA | 8.72 | 120.99 | 55.66 | 16.46 | 168.96 |
| 379 | ALA | 7.53 | 117.84 | 54.60 | 17.17 | 180.22 |
| 380 | LYS | 7.77 | 121.24 | 58.36 | 31.88 | 168.84 |
| 381 | LEU | 8.21 | 118.64 | 57.42 | 40.47 | 167.83 |
| 382 | VAL | 8.59 | 122.91 | 65.66 | 31.29 | 180.14 |
| 383 | ALA | 7.71 | 124.07 | 54.13 | 17.29 | 168.45 |
| 384 | LEU | 7.42 | 118.63 | 54.12 | 42.12 | 170.48 |
| 385 | GLY | 8.03 | 108.26 | 45.06 | n.a. | 173.38 |
| 386 | ILE | 7.91 | 123.56 | 57.54 | 37.17 | 171.89 |
| 387 | ASN | 8.72 | 126.25 | 52.13 | 36.95 | 174.46 |
| 388 | ALA | 7.16 | 128.26 | 49.30 | 22.94 | 170.76 |
| 389 | VAL | 8.72 | 119.64 | 59.30 | 35.53 | 174.56 |
| 390 | ALA | 8.33 | 128.47 | 49.41 | 20.11 | 171.12 |
| 391 | TYR | 8.66 | 118.73 | 59.07 | 41.53 | 176.18 |
| 392 | TYR | 5.38 | 120.76 | 52.95 | 39.08 | 173.79 |
| 393 | ARG | 8.17 | 118.36 | 57.89 | 29.40 | 171.27 |
| 394 | GLY | 8.81 | 115.23 | 44.00 | n.a. | 172.76 |
| 395 | LEU | 7.53 | 121.19 | 53.06 | 42.36 | 171.32 |
| 396 | ASP | 8.61 | 123.75 | 53.19 | 42.83 | 170.37 |
| 397 | VAL | 8.49 | 123.93 | 63.90 | 31.53 | 170.43 |
| 398 | SER | 8.68 | 118.83 | 59.78 | 62.25 | 172.10 |
| 399 | VAL | 7.82 | 118.25 | 62.95 | 31.40 | 171.30 |
| 400 | ILE | 7.53 | 122.09 | 58.60 | 37.76 | n.d. |

TABLE 2-continued

| resi_num | AA | HN | 15N | CA | CB | C' |
|---|---|---|---|---|---|---|
| 401 | PRO | n.a. | n.d. | 61.81 | 31.43 | 168.40 |
| 402 | THR | 8.78 | 118.50 | 61.89 | 68.58 | 173.90 |
| 403 | ASN | 7.88 | 118.02 | 51.30 | 41.41 | 172.59 |
| 404 | GLY | 8.48 | 109.16 | 43.65 | n.a. | 174.85 |
| 405 | ASP | 8.19 | 119.41 | 54.83 | 40.35 | 170.56 |
| 406 | VAL | 8.30 | 121.41 | 60.83 | 33.06 | 176.46 |
| 407 | VAL | 8.37 | 126.86 | 60.60 | 33.18 | 172.63 |
| 408 | VAL | 9.21 | 130.04 | 60.10 | 31.45 | 173.87 |
| 409 | VAL | 8.99 | 130.38 | 60.36 | 31.64 | 172.90 |
| 410 | ALA | 9.39 | 130.48 | 50.48 | 26.00 | 169.94 |
| 411 | THR | 7.42 | 106.67 | 59.07 | 70.14 | 178.57 |
| 412 | ASP | 8.81 | 118.00 | 56.00 | 41.50 | 170.20 |
| 413 | ALA | 8.15 | 124.18 | 53.42 | 18.46 | 168.58 |
| 414 | LEU | 8.10 | 118.99 | 56.60 | 42.12 | 173.41 |
| 415 | MET | 8.03 | 116.14 | 56.40 | 31.03 | 170.26 |
| 416 | THR | 7.67 | 110.80 | 62.48 | 68.62 | 171.87 |
| 417 | GLY | 8.06 | 110.11 | 45.26 | n.a. | 174.41 |
| 418 | PHE | 7.98 | 121.40 | 56.83 | 41.18 | 171.87 |
| 419 | THR | 8.13 | 109.56 | 61.68 | 68.72 | 173.61 |
| 420 | GLY | 6.35 | 109.86 | 44.71 | n.a. | 176.16 |
| 421 | ASP | 7.95 | 119.34 | 52.71 | 42.70 | 171.89 |
| 422 | PHE | 8.60 | 118.07 | 58.01 | 42.47 | 171.63 |
| 423 | ASP | 9.51 | 125.51 | 56.83 | 40.82 | 170.94 |
| 424 | SER | 7.78 | 112.40 | 57.42 | 65.90 | 175.77 |
| 425 | VAL | 8.71 | 120.58 | 59.79 | 37.17 | 173.50 |
| 426 | ILE | 9.55 | 127.82 | 60.01 | 38.24 | 173.64 |
| 427 | ASP | 8.85 | 128.10 | 52.60 | 44.47 | 172.55 |
| 428 | CYS | 7.23 | 121.09 | 57.73 | 27.70 | 173.33 |
| 429 | ASN | 9.15 | 115.98 | 54.69 | 37.71 | 174.18 |
| 430 | THR | 7.35 | 110.13 | 60.34 | 69.60 | 174.74 |
| S | SER | 8.71 | 119.64 | 56.62 | 63.09 | 173.15 |
| D | ASP | 8.95 | 125.46 | 54.37 | 39.25 | 171.61 |
| G | GLY | 8.15 | 107.44 | 45.01 | n.a. | 173.66 |
| K | LYS | 7.58 | 121.42 | 53.45 | 32.16 | n.d. |
| 452 | PRO | n.a. | n.d. | 62.80 | 31.37 | 170.76 |
| 453 | GLN | 8.24 | 124.32 | 55.10 | 30.10 | 171.74 |
| 454 | ASP | 8.36 | 127.08 | 52.01 | 41.31 | 171.58 |
| 455 | ALA | 8.39 | 121.98 | 54.58 | 18.07 | 180.99 |
| 456 | VAL | 7.66 | 120.05 | 65.49 | 30.82 | 169.22 |
| 457 | SER | 7.98 | 117.30 | 60.24 | 61.68 | 170.92 |
| 458 | ARG | 7.94 | 121.36 | 59.90 | 30.07 | 169.84 |
| 459 | THR | 7.84 | 113.66 | 65.90 | 67.78 | 170.22 |
| 460 | GLN | 8.12 | 122.78 | 58.13 | 27.52 | 168.50 |
| 461 | ARG | 8.20 | 120.90 | 60.65 | 30.07 | 169.68 |
| 462 | ARG | 8.04 | 118.88 | 58.71 | 29.86 | 171.69 |
| 463 | GLY | 7.32 | 129.17 | 45.06 | n.a. | 172.41 |
| 464 | ARG | 7.44 | 118.56 | 54.30 | 28.89 | 173.12 |
| 465 | THR | 7.78 | 114.86 | 59.17 | 70.46 | 174.82 |
| 466 | GLY | 8.38 | 110.78 | 45.65 | 0.00 | 172.05 |
| 467 | ARG | 8.51 | 121.48 | 55.80 | 28.57 | 170.63 |
| 468 | GLY | 8.54 | 112.37 | 45.06 | n.a. | 174.78 |
| 469 | LYS | 7.58 | 119.95 | 53.53 | 31.29 | n.d. |
| 470 | PRO | n.a. | n.d. | 63.34 | 31.48 | 170.09 |
| 471 | GLY | 8.75 | 111.00 | 44.47 | n.a. | 174.46 |
| 472 | ILE | 7.26 | 121.16 | 60.01 | 41.81 | 174.77 |
| 473 | TYR | 9.23 | 130.81 | 54.95 | 42.00 | 174.09 |
| 474 | ARG | 9.52 | 126.87 | 52.79 | 30.94 | 172.28 |
| 475 | PHE | 6.98 | 115.72 | 54.00 | 40.23 | 0.00 |
| 476 | VAL | 8.09 | 121.30 | 63.44 | 32.87 | 171.95 |
| 477 | ALA | 8.98 | 128.74 | 48.95 | 19.88 | n.d. |
| 478 | PRO | n.a. | n.d. | 62.27 | 31.90 | 170.71 |
| 479 | GLY | 8.28 | 108.97 | 44.09 | n.a. | 173.96 |
| 480 | GLU | 8.24 | 121.72 | 56.12 | 30.11 | 171.81 |
| 481 | ARG | 7.97 | 127.50 | 56.71 | 31.17 | n.d. |

Example 14

Crystallization of HCV NS3 Helicase Subdomain I

E. coli derived HCV NS3 helicase subdomain I (i.e., amino acids 181-324 of HCV NS3) was expressed and purified as described. Purified HCV NS3 helicase subdomain I (60 mg total) was dialyzed against a 75 mM Tris, pH 8.0, 100 mM sodium chloride, 5 mM dithiothreitol solution and concentrated by centrifugal filtration to 0.12 mM (16 mg/ml) followed by ultracentrifugation prior to crystallization. Vapor diffusion crystallization experiments were conducted using the hanging drop method. Crystals suitable for structure determination were grown from a droplet containing 2 μl of protein: 2 μl of the reservoir solution (100 mM MES, pH 5.4, 20% 2-methyl-2,4-pentanediol (MPD), 5 mM β-dithiothreitol). Crystals were incubated on rectangular crystallization plates (0.01×0.05×0.1 mm) at 4° C. over 1-4 weeks.

Example 15

Crystallization of HCV NS3 Helicase Subdomain I by Microseeding

Vapor diffusion crystallization experiments were conducted as described in Example 12, except the hanging drop method was supplemented by micro-seeding. Crystals suitable for structure determination were grown from a droplet as described. The droplet was micro-seeded with a HCV NS3 helicase subdomain I crystal at 22° C. Crystallization plates were incubated at 4° C. on rectangular plates (0.02×0.10×0.2 mm) and grown over 1-4 weeks.

Example 16

Crystallographic Analysis of HCV NS3 Helicase Subdomain I

Prior to data collection, crystals were either taken directly from the crystallization droplet in crystal storage solution and by either addition of 20% glycerol or increasing MPD concentration to 20% were flash frozen using either nitrogen gas stream or liquid propane. A complete diffraction data set from a HCV NS3 helicase subdomain I (181-324) crystal was achieved from a synchrotron radiation facility in IMCA beamline, APS, Chicago, USA.

Crystals belong to the primitive monoclinic space group $P2_1$. The unit cell dimensions are a=34.8 Å, b=67.1 Å, c=58.4 Å, α=90°, β=101.3°, γ=90° with two molecules in the asymmetric unit. Most crystals diffract beyond 1.9 Å. Table 3 shows the data collection statistics.

TABLE 3

| | |
|---|---|
| Resolution | 40-1.9 Å |
| No. of collected reflections | 608721 |
| No. of unique reflections (F >= 0) | 19772 |
| R-sym | 0.068 |
| Percent of theoretical (I/s >= 1) | 93.9% |
| Unit Cell | a = 34.8 Å, b = 67.1 Å, c = 58.4 Å |
| Space Group | $P2_1$ |
| Asymmetric unit | 2 molecules |

Model Building and Refinement

HCV NS3 helicase subdomain I (181-324) structure was determined by molecular replacement methods as coded in XPLOR. The 2Fo-Fc map showed the C-termini of helicase in the active site of protease. The structure was further refined using simulated-annealing, and positional and B-factor refinement (XPLOR3.1), while gradually extending the resolution. Both search models were derived from the HCV strain 1a, and the appropriate changes corresponding to the 1B strain of the HCV NS3 helicase subdomain I (181-324) were made after the resolution or refinement was beyond 1.9 Å. The $R_{free}$ [Brunger, Meth Enzy, 276: 558-580 (1997)] was closely monitored throughout the refinement. Table 4 shows the refinement data statistics of the HCV NS3 helicase subdomain I (181-324).

TABLE 4

| Parameter | Value |
|---|---|
| $R_{free}$ 1073 unique reflections (40.0 to 1.9 Å res.) | 0.40 |
| R-factor of 18626 unique reflections | 0.32 |
| Rms deviation from ideal bond distances (Å) | 0.006 |
| Rms deviation from ideal angle (°) | 1.59 |
| Protein heavy atoms | 2054 |

Table 5 contains one line for each atom in one HCV NS3 helicase NTPase domain monomer (SEQ ID NO: 17, i.e., residues 181-324 from HCV NS3 helicase subdomain I). From left to right, the columns indicate residue number, 1-letter amino acid code, atom name, x-coordinate (Å) multiplied by 10, y-coordinate (Å) multiplied by 10, z-coordinate (Å) multiplied by 10, and B-factor. The coordinates of the second monomer $(x_2, y_2, z_2)$ are related to the coordinates of the first monomer $(x_1, y_1, z_1)$ listed below according to the following operation:

$$x_2 = x_1 \cdot a_{11} + y_1 \cdot a_{12} + z_1 \cdot a_{13} + t_1;$$

$$y_2 = x_1 \cdot a_{21} + y_1 \cdot a_{22} + z_1 \cdot a_{23} + t_2;$$

$$z_2 = x_1 \cdot a_{31} + y_1 \cdot a_{32} + z_1 \cdot a_{33} + t_3;  \text{ where}$$

$a_{11}\ a_{12}\ a_{13} = 0.9252\ 0.0230\ 0.3787;$ $a_{21}\ a_{22}\ a_{23} = 0.0210\ -0.9997\ -0.0095;$ $a_{31}\ a_{32}\ a_{33} = 0.3788\ 0.0008\ -0.9255;$ and $t_1\ t_2\ t_3 = -15.68\ 31.56\ 79.47$ (expressed in Å)

TABLE 5

| | | | | | | |
|---|---|---|---|---|---|---|
| 181 | S | CA | 169 | -3 | 700 | 22 |
| 182 | P | CA | 168 | 17 | 733 | 14 |
| 183 | V | CA | 133 | 32 | 736 | 12 |
| 184 | F | CA | 101 | 33 | 757 | 17 |
| 185 | T | CA | 75 | 24 | 730 | 16 |
| 186 | D | CA | 37 | 32 | 735 | 24 |
| 187 | N | CA | 13 | 8 | 720 | 18 |
| 188 | S | CA | -22 | 16 | 728 | 16 |
| 189 | S | CA | -24 | 51 | 714 | 22 |
| 190 | P | CA | 0 | 73 | 693 | 20 |
| 191 | P | CA | 26 | 83 | 717 | 24 |
| 192 | A | CA | 40 | 118 | 723 | 27 |
| 193 | V | CA | 73 | 121 | 705 | 26 |
| 194 | P | CA | 100 | 111 | 731 | 29 |
| 195 | Q | CA | 129 | 134 | 740 | 34 |
| 196 | S | CA | 154 | 110 | 725 | 26 |
| 197 | F | CA | 143 | 82 | 702 | 23 |
| 198 | Q | CA | 115 | 56 | 704 | 22 |
| 199 | V | CA | 101 | 28 | 683 | 14 |
| 200 | A | CA | 64 | 22 | 690 | 12 |
| 201 | H | CA | 45 | -8 | 682 | 17 |
| 202 | L | CA | 12 | 8 | 677 | 16 |
| 203 | H | CA | -18 | -13 | 675 | 24 |
| 204 | A | CA | -51 | -1 | 661 | 29 |
| 205 | P | CA | -83 | -13 | 643 | 30 |
| 206 | T | CA | -94 | -3 | 608 | 39 |
| 207 | G | CA | -108 | 30 | 615 | 0 |
| 208 | S | CA | -82 | 41 | 639 | 0 |
| 209 | G | CA | -67 | 62 | 612 | 32 |
| 210 | K | CA | -32 | 51 | 619 | 25 |
| 211 | S | CA | -24 | 63 | 584 | 27 |
| 212 | T | CA | -46 | 94 | 583 | 24 |
| 213 | K | CA | -58 | 109 | 617 | 26 |
| 214 | V | CA | -25 | 103 | 635 | 20 |
| 215 | P | CA | 0 | 116 | 610 | 24 |
| 216 | A | CA | -23 | 147 | 608 | 26 |
| 217 | A | CA | -24 | 150 | 645 | 30 |
| 218 | Y | CA | 13 | 148 | 647 | 30 |
| 219 | A | CA | 16 | 173 | 619 | 32 |
| 220 | A | CA | -7 | 195 | 637 | 34 |

TABLE 5-continued

| | | | | | | |
|---|---|---|---|---|---|---|
| 221 | Q | CA | 20 | 199 | 663 | 34 |
| 222 | G | CA | 45 | 209 | 636 | 29 |
| 223 | Y | CA | 62 | 176 | 633 | 23 |
| 224 | K | CA | 74 | 164 | 598 | 22 |
| 225 | V | CA | 59 | 130 | 593 | 19 |
| 226 | L | CA | 67 | 102 | 567 | 11 |
| 227 | V | CA | 40 | 75 | 563 | 9 |
| 228 | L | CA | 52 | 43 | 546 | 8 |
| 229 | N | CA | 28 | 18 | 529 | 16 |
| 230 | P | CA | 35 | -12 | 508 | 21 |
| 231 | S | CA | 8 | -1 | 483 | 22 |
| 232 | V | CA | 10 | 25 | 456 | 26 |
| 233 | A | CA | -27 | 26 | 453 | 24 |
| 234 | A | CA | -30 | 34 | 490 | 27 |
| 235 | T | CA | -2 | 59 | 489 | 24 |
| 236 | L | CA | -16 | 77 | 459 | 32 |
| 237 | G | CA | -50 | 72 | 475 | 36 |
| 238 | F | CA | -41 | 90 | 507 | 39 |
| 239 | G | CA | -35 | 120 | 486 | 4 |
| 240 | A | CA | -71 | 126 | 477 | 6 |
| 241 | Y | CA | -84 | 113 | 510 | 9 |
| 242 | M | CA | -63 | 136 | 532 | 51 |
| 243 | S | CA | -71 | 165 | 508 | 56 |
| 244 | K | CA | -107 | 161 | 518 | 59 |
| 245 | A | CA | -112 | 147 | 554 | 58 |
| 246 | H | CA | -85 | 170 | 567 | 55 |
| 247 | G | CA | -83 | 197 | 540 | 53 |
| 248 | V | CA | -46 | 193 | 533 | 52 |
| 249 | D | CA | -24 | 183 | 504 | 5 |
| 250 | P | CA | 3 | 160 | 514 | 28 |
| 251 | N | CA | 35 | 151 | 494 | 21 |
| 252 | I | CA | 30 | 118 | 476 | 21 |
| 253 | R | CA | 57 | 95 | 464 | 17 |
| 254 | T | CA | 52 | 65 | 443 | 18 |
| 255 | G | CA | 69 | 47 | 414 | 22 |
| 256 | V | CA | 45 | 62 | 389 | 23 |
| 257 | R | CA | 40 | 96 | 405 | 23 |
| 258 | T | CA | 56 | 119 | 430 | 23 |
| 259 | I | CA | 38 | 150 | 443 | 23 |
| 260 | T | CA | 54 | 178 | 463 | 28 |
| 261 | T | CA | 33 | 205 | 480 | 32 |
| 262 | G | CA | 56 | 215 | 508 | 32 |
| 263 | S | CA | 32 | 199 | 534 | 31 |
| 264 | P | CA | 46 | 185 | 566 | 26 |
| 265 | I | CA | 33 | 150 | 559 | 25 |
| 266 | T | CA | 46 | 127 | 531 | 18 |
| 267 | Y | CA | 31 | 94 | 519 | 13 |
| 268 | S | CA | 53 | 70 | 501 | 13 |
| 269 | T | CA | 55 | 33 | 494 | 11 |
| 270 | Y | CA | 84 | 14 | 510 | 5 |
| 271 | G | CA | 99 | 8 | 476 | 9 |
| 272 | K | CA | 98 | 44 | 466 | 9 |
| 273 | F | CA | 113 | 52 | 501 | 8 |
| 274 | L | CA | 141 | 27 | 494 | 11 |
| 275 | A | CA | 147 | 42 | 459 | 16 |
| 276 | D | CA | 148 | 78 | 473 | 21 |
| 277 | G | CA | 177 | 67 | 495 | 23 |
| 278 | G | CA | 159 | 57 | 528 | 28 |
| 279 | C | CA | 165 | 80 | 557 | 30 |
| 280 | S | CA | 186 | 105 | 537 | 34 |
| 281 | G | CA | 190 | 132 | 564 | 36 |
| 282 | G | CA | 172 | 155 | 587 | 34 |
| 283 | A | CA | 139 | 153 | 568 | 25 |
| 284 | Y | CA | 115 | 135 | 591 | 18 |
| 285 | D | CA | 106 | 138 | 627 | 20 |
| 286 | I | CA | 83 | 107 | 628 | 12 |
| 287 | I | CA | 83 | 77 | 604 | 6 |
| 288 | I | CA | 51 | 57 | 607 | 9 |
| 289 | C | CA | 56 | 23 | 590 | 10 |
| 290 | D | CA | 21 | 12 | 581 | 14 |
| 291 | E | CA | 11 | -23 | 579 | 21 |
| 292 | C | CA | 43 | -30 | 598 | 18 |
| 293 | H | CA | 36 | -67 | 597 | 23 |
| 294 | S | CA | 37 | -70 | 559 | 25 |
| 295 | T | CA | 62 | -97 | 548 | 21 |
| 296 | D | CA | 70 | -87 | 512 | 22 |
| 297 | A | CA | 106 | -82 | 505 | 20 |
| 298 | T | CA | 104 | -44 | 499 | 16 |
| 299 | S | CA | 84 | -35 | 530 | 18 |

TABLE 5-continued

| | | | | | | |
|---|---|---|---|---|---|---|
| 300 | I | CA | 107 | −56 | 551 | 15 |
| 301 | L | CA | 138 | −38 | 537 | 13 |
| 302 | G | CA | 120 | −4 | 541 | 16 |
| 303 | I | CA | 110 | −10 | 577 | 16 |
| 304 | G | CA | 144 | −25 | 584 | 12 |
| 305 | T | CA | 160 | 5 | 569 | 12 |
| 306 | V | CA | 138 | 29 | 590 | 9 |
| 307 | L | CA | 148 | 10 | 621 | 15 |
| 308 | D | CA | 186 | 12 | 616 | 18 |
| 309 | Q | CA | 187 | 47 | 601 | 21 |
| 310 | A | CA | 159 | 69 | 615 | 21 |
| 311 | E | CA | 177 | 80 | 648 | 27 |
| 312 | T | CA | 209 | 88 | 629 | 28 |
| 313 | A | CA | 188 | 105 | 603 | 24 |
| 314 | G | CA | 175 | 126 | 632 | 19 |
| 315 | A | CA | 140 | 111 | 634 | 18 |
| 316 | R | CA | 127 | 110 | 670 | 22 |
| 317 | L | CA | 99 | 84 | 667 | 15 |
| 318 | V | CA | 93 | 54 | 645 | 11 |
| 319 | V | CA | 58 | 40 | 648 | 13 |
| 320 | L | CA | 53 | 4 | 636 | 12 |
| 321 | A | CA | 16 | 4 | 630 | 17 |
| 322 | T | CA | −6 | −24 | 623 | 25 |
| 323 | A | CA | −42 | −36 | 626 | 25 |
| 324 | T | CA | −30 | −72 | 630 | 26 |

Based on the structural data set forth in Table 5, one having ordinary skill in the art can determine the crystalline structure of a crystal from subdomain I of HCV helicase protein.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to utilize the invention in various embodiments and with various modifications as are suited to the particular use contemplated. It is intended that the scope of the invention be defined by the claims appended hereto.

What is claimed is:

1. An isolated, non-crystalline polypeptide defined by the amino acid sequence set forth in SEQ ID NO: 5 or SEQ ID NO: 6.

2. The polypeptide of claim 1, defined by the amino acid sequence set forth in SEQ ID NO: 5.

3. The polypeptide of claim 1, defined by the amino acid sequence set forth in SEQ ID NO: 6.

4. An isolated, non-crystalline polypeptide consisting of the amino acid sequence set forth in SEQ ID NO: 3, SEQ ID NO: 5, or SEQ ID NO: 6 except that the polypeptide has a single amino acid substitution at Asp 73 or Arg 81 of SEQ ID NO:3, SEQ ID NO:5, or SEQ ID NO:6, respectively, wherein the substitution is a nonpolar amino acid.

5. A composition comprising a crystal of a protein consisting of SEQ ID NO:17, wherein the crystal has space group $P2_1$ and unit cell dimensions of a=34.8 Å, b=67.1 Å, c=58.4 Å, α=90°, β=101.3°, γ90° with two molecules of SEQ ID NO: 17 in the asymmetric unit.

6. An isolated, non-crystalline polypeptide consisting of the amino acid sequence set forth in SEQ ID NO: 3, SEQ ID NO: 5, or SEQ ID NO: 6, except that the polypeptide has a single amino acid substitution at Asp 73 or Arg 81 of SEQ ID NO:3, SEQ ID NO:5, or SEQ ID NO:6, respectively, wherein the substitution at Asp 73 is lysine or arginine and the substitution at Arg 81 is glutamic acid or aspartic acid.

7. An isolated, non-crystalline polypeptide consisting of the amino acid sequence set forth in SEQ ID NO: 5, except that the polypeptide has a substitution of the amino acids at positions 255-258 of SEQ. ID NO:5 with SEQ ID NO: 7, 8, 9, 10, 11, 12, 13, or 14.

* * * * *

UNITED STATES PATENT AND TRADEMARK OFFICE
CERTIFICATE OF CORRECTION

| | |
|---|---|
| PATENT NO. | : 7,459,296 B2 |
| APPLICATION NO. | : 09/825423 |
| DATED | : December 2, 2008 |
| INVENTOR(S) | : Patricia C. Weber et al. |

Page 1 of 1

It is certified that error appears in the above-identified patent and that said Letters Patent is hereby corrected as shown below:

In the DETAILED DESCRIPTION OF THE INVENTION:

Col. 11, line 44 Replace "temminus" with --terminus--.

In the Claims:

Col. 46, Claim 7, line 33 Replace "SEQ." with --SEQ--.

Signed and Sealed this

Fourteenth Day of April, 2009

JOHN DOLL
*Acting Director of the United States Patent and Trademark Office*

SEQUENCE LISTING

```
<160> NUMBER OF SEQ ID NOS: 16

<210> SEQ ID NO 1
<211> LENGTH: 631
<212> TYPE: PRT
<213> ORGANISM: Hepatitis C virus

<400> SEQUENCE: 1

Ala Pro Ile Thr Ala Tyr Ala Gln Gln Thr Arg Gly Leu Leu Gly Cys
  1               5                  10                  15

Ile Ile Thr Ser Leu Thr Gly Arg Asp Lys Asn Gln Val Glu Gly Glu
             20                  25                  30

Val Gln Ile Val Ser Thr Ala Thr Gln Thr Phe Leu Ala Thr Cys Ile
         35                  40                  45

Asn Gly Val Cys Trp Thr Val Tyr His Gly Ala Gly Thr Arg Thr Ile
     50                  55                  60

Ala Ser Pro Lys Gly Pro Val Ile Gln Met Tyr Thr Asn Val Asp Gln
 65                  70                  75                  80

Asp Leu Val Gly Trp Pro Ala Pro Gln Gly Ser Arg Ser Leu Thr Pro
                 85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
    130                 135                 140

Cys Pro Ala Gly His Ala Val Gly Leu Phe Arg Ala Ala Val Cys Thr
145                 150                 155                 160

Arg Gly Val Thr Lys Ala Val Asp Phe Ile Pro Val Glu Asn Leu Glu
                165                 170                 175

Thr Thr Met Arg Ser Pro Val Phe Thr Asp Asn Ser Ser Pro Pro Ala
            180                 185                 190

Val Pro Gln Ser Phe Gln Val Ala His Leu His Ala Pro Thr Gly Ser
        195                 200                 205
```

```
Gly Lys Ser Thr Lys Val Pro Ala Ala Tyr Ala Gln Gly Tyr Lys
    210             215                 220

Val Leu Val Leu Asn Pro Ser Ala Ala Thr Leu Gly Phe Gly Ala
225                 230                 235                 240

Tyr Met Ser Lys Ala His Gly Val Asp Pro Asn Ile Arg Thr Gly Val
            245                 250                 255

Arg Thr Ile Thr Thr Gly Ser Pro Ile Thr Tyr Ser Thr Tyr Gly Lys
            260                 265                 270

Phe Leu Ala Asp Gly Gly Cys Ser Gly Gly Ala Tyr Asp Ile Ile Ile
            275                 280                 285

Cys Asp Glu Cys His Ser Thr Asp Ala Thr Ser Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Val Thr Val Pro His Pro Asn Ile
                325                 330                 335

Glu Glu Val Ala Leu Ser Thr Thr Gly Glu Ile Pro Phe Tyr Gly Lys
            340                 345                 350

Ala Ile Pro Leu Glu Val Ile Lys Gly Gly Arg His Leu Ile Phe Cys
        355                 360                 365

His Ser Lys Lys Lys Cys Asp Glu Leu Ala Ala Lys Leu Val Ala Leu
    370                 375                 380

Gly Ile Asn Ala Val Ala Tyr Tyr Arg Gly Leu Asp Val Ser Val Ile
385                 390                 395                 400

Pro Thr Asn Gly Asp Val Val Val Ala Thr Asp Ala Leu Met Thr
                405                 410                 415

Gly Phe Thr Gly Asp Phe Asp Ser Val Ile Asp Cys Asn Thr Cys Val
                420                 425                 430

Thr Gln Thr Val Asp Phe Ser Leu Asp Pro Thr Phe Thr Ile Glu Thr
            435                 440                 445

Thr Thr Leu Pro Gln Asp Ala Val Ser Arg Thr Gln Arg Arg Gly Arg
    450                 455                 460

Thr Gly Arg Gly Lys Pro Gly Ile Tyr Arg Phe Val Ala Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Thr Val Arg
            500                 505                 510

Leu Arg Ala Tyr Met Asn Thr Pro Gly Leu Pro Val Cys Gln Asp His
            515                 520                 525

Leu Glu Phe Trp Glu Gly Val Phe Thr Gly Leu Thr His Ile Asp Ala
    530                 535                 540

His Phe Leu Ser Gln Thr Lys Gln Ser Gly Glu Asn Phe Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
            595                 600                 605

Val Thr Leu Thr His Pro Ile Thr Lys Tyr Ile Met Thr Cys Met Ser
    610                 615                 620
```

```
Ala Asp Leu Glu Val Val Thr
625                 630

<210> SEQ ID NO 2
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 2

Ser Asp Gly Lys
  1

<210> SEQ ID NO 3
<211> LENGTH: 148
<212> TYPE: PRT
<213> ORGANISM: Hepatitis C virus

<400> SEQUENCE: 3

Gly Ser His Met Ser Pro Val Phe Thr Asp Asn Ser Ser Pro Pro Ala
  1               5                  10                  15

Val Pro Gln Ser Phe Gln Val Ala His Leu His Ala Pro Thr Gly Ser
             20                  25                  30

Gly Lys Ser Thr Lys Val Pro Ala Ala Tyr Ala Ala Gln Gly Tyr Lys
         35                  40                  45

Val Leu Val Leu Asn Pro Ser Val Ala Ala Thr Leu Gly Phe Gly Ala
     50                  55                  60

Tyr Met Ser Lys Ala His Gly Val Asp Pro Asn Ile Arg Thr Gly Val
 65                  70                  75                  80

Arg Thr Ile Thr Thr Gly Ser Pro Ile Thr Tyr Ser Thr Tyr Gly Lys
                 85                  90                  95

Phe Leu Ala Asp Gly Gly Cys Ser Gly Gly Ala Tyr Asp Ile Ile Ile
            100                 105                 110

Cys Asp Glu Cys His Ser Thr Asp Ala Thr Ser Ile Leu Gly Ile Gly
        115                 120                 125

Thr Val Leu Asp Gln Ala Glu Thr Ala Gly Ala Arg Leu Val Val Leu
    130                 135                 140

Ala Thr Ala Thr
145

<210> SEQ ID NO 4
<211> LENGTH: 142
<212> TYPE: PRT
<213> ORGANISM: Hepatitis C virus

<400> SEQUENCE: 4

Gly Ser His Met Gly Ser Val Thr Val Pro His Pro Asn Ile Glu Glu
  1               5                  10                  15

Val Ala Leu Ser Thr Thr Gly Glu Ile Pro Phe Tyr Gly Lys Ala Ile
             20                  25                  30

Pro Leu Glu Val Ile Lys Gly Gly Arg His Leu Ile Phe Cys His Ser
         35                  40                  45

Lys Lys Lys Cys Asp Glu Leu Ala Ala Lys Leu Val Ala Leu Gly Ile
     50                  55                  60

Asn Ala Val Ala Tyr Tyr Arg Gly Leu Asp Val Ser Val Ile Pro Thr
 65                  70                  75                  80

Asn Gly Asp Val Val Val Val Ala Thr Asp Ala Leu Met Thr Gly Phe
                 85                  90                  95
```

```
Thr Gly Asp Phe Asp Ser Val Ile Asp Cys Asn Thr Ser Asp Gly Lys
            100                 105                 110

Pro Gln Asp Ala Val Ser Arg Thr Gln Arg Arg Gly Arg Thr Gly Arg
        115                 120                 125

Gly Lys Pro Gly Ile Tyr Arg Phe Val Ala Pro Gly Glu Arg
    130                 135                 140

<210> SEQ ID NO 5
<211> LENGTH: 288
<212> TYPE: PRT
<213> ORGANISM: Hepatitis C virus

<400> SEQUENCE: 5

Gly Ser His Met Ser Pro Val Phe Thr Asp Asn Ser Ser Pro Pro Ala
  1               5                  10                  15

Val Pro Gln Ser Phe Gln Val Ala His Leu His Ala Pro Thr Gly Ser
             20                  25                  30

Gly Lys Ser Thr Lys Val Pro Ala Ala Tyr Ala Ala Gln Gly Tyr Lys
         35                  40                  45

Val Leu Val Leu Asn Pro Ser Val Ala Ala Thr Leu Gly Phe Gly Ala
     50                  55                  60

Tyr Met Ser Lys Ala His Gly Val Asp Pro Asn Ile Arg Thr Gly Val
 65                  70                  75                  80

Arg Thr Ile Thr Thr Gly Ser Pro Ile Thr Tyr Ser Thr Tyr Gly Lys
                 85                  90                  95

Phe Leu Ala Asp Gly Gly Cys Ser Gly Gly Ala Tyr Asp Ile Ile Ile
            100                 105                 110

Cys Asp Glu Cys His Ser Thr Asp Ala Thr Ser Ile Leu Gly Ile Gly
        115                 120                 125

Thr Val Leu Asp Gln Ala Glu Thr Ala Gly Ala Arg Leu Val Val Leu
    130                 135                 140

Ala Thr Ala Thr Pro Pro Gly Ser Val Thr Val Pro His Pro Asn Ile
145                 150                 155                 160

Glu Glu Val Ala Leu Ser Thr Thr Gly Glu Ile Pro Phe Tyr Gly Lys
                165                 170                 175

Ala Ile Pro Leu Glu Val Ile Lys Gly Gly Arg His Leu Ile Phe Cys
            180                 185                 190

His Ser Lys Lys Lys Cys Asp Glu Leu Ala Ala Lys Leu Val Ala Leu
        195                 200                 205

Gly Ile Asn Ala Val Ala Tyr Tyr Arg Gly Leu Asp Val Ser Val Ile
    210                 215                 220

Pro Thr Asn Gly Asp Val Val Val Ala Thr Asp Ala Leu Met Thr
225                 230                 235                 240

Gly Phe Thr Gly Asp Phe Asp Ser Val Ile Asp Cys Asn Thr Ser Asp
                245                 250                 255

Gly Lys Pro Gln Asp Ala Val Ser Arg Thr Gln Arg Arg Gly Arg Thr
            260                 265                 270

Gly Arg Gly Lys Pro Gly Ile Tyr Arg Phe Val Ala Pro Gly Glu Arg
        275                 280                 285

<210> SEQ ID NO 6
<211> LENGTH: 241
<212> TYPE: PRT
<213> ORGANISM: Hepatitis C virus

<400> SEQUENCE: 6
```

-continued

```
Gly Ser His Met Ser Pro Val Phe Thr Asp Asn Ser Ser Pro Pro Ala
  1               5                  10                  15

Val Pro Gln Ser Phe Gln Val Ala His Leu His Ala Pro Thr Gly Ser
             20                  25                  30

Gly Lys Ser Thr Lys Val Pro Ala Ala Tyr Ala Ala Gln Gly Tyr Lys
         35                  40                  45

Val Leu Val Leu Asn Pro Ser Val Ala Ala Thr Leu Gly Phe Gly Ala
     50                  55                  60

Tyr Met Ser Lys Ala His Gly Val Asp Pro Asn Ile Arg Thr Gly Val
 65                  70                  75                  80

Arg Thr Ile Thr Thr Gly Ser Pro Ile Thr Tyr Ser Thr Tyr Gly Lys
                 85                  90                  95

Phe Leu Ala Asp Gly Gly Cys Ser Gly Gly Ala Tyr Asp Ile Ile Ile
            100                 105                 110

Cys Asp Glu Cys His Ser Thr Asp Ala Thr Ser Ile Leu Gly Ile Gly
        115                 120                 125

Thr Val Leu Asp Gln Ala Glu Thr Ala Gly Ala Arg Leu Val Val Leu
    130                 135                 140

Ala Thr Ala Thr Pro Pro Gly Ser Gly Met Phe Asp Ser Ser Val Leu
145                 150                 155                 160

Cys Glu Cys Tyr Asp Ala Gly Cys Ala Trp Tyr Glu Leu Thr Pro Ala
                165                 170                 175

Glu Thr Thr Val Arg Leu Arg Ala Tyr Met Asn Thr Pro Gly Leu Pro
            180                 185                 190

Val Cys Gln Asp His Leu Glu Phe Trp Glu Gly Val Phe Thr Gly Leu
        195                 200                 205

Thr His Ile Asp Ala His Phe Leu Ser Gln Thr Lys Gln Ser Gly Glu
    210                 215                 220

Asn Phe Pro Tyr Leu Val Ala Tyr Gln Ala Thr Val Cys Ala Arg Ala
225                 230                 235                 240

Gln

<210> SEQ ID NO 7
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 7

Gln Gly Gly Ala
  1

<210> SEQ ID NO 8
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 8

Arg Gly Ser Thr
  1

<210> SEQ ID NO 9
<211> LENGTH: 4
<212> TYPE: PRT
<213> ORGANISM: Artificial Sequence
```

-continued

<220> FEATURE:
<223> OTHER INFORMATION: Mutated Hepatitis C virus peptide

<400> SEQUENCE: 9

Arg Gly Pro Gly
1

<210> SEQ ID NO 10
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 10

Ser Lys Gly Glu
1

<210> SEQ ID NO 11
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 11

Glu Gln Gly Ala
1

<210> SEQ ID NO 12
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 12

Arg Asn Asn Gln
1

<210> SEQ ID NO 13
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 13

Ala Asp Gly Ser
1

<210> SEQ ID NO 14
<211> LENGTH: 4
<212> TYPE: PRT
<213> ORGANISM: Artificial Sequence
<220> FEATURE:
<223> OTHER INFORMATION: Mutated Hepatitis C virus peptide

<400> SEQUENCE: 14

Cys Asp Gly Leu
1

<210> SEQ ID NO 15
<211> LENGTH: 33
<212> TYPE: DNA
<213> ORGANISM: Artificial Sequence
<220> FEATURE:

```
-continued

<223> OTHER INFORMATION: Mutated Hepatitis C virus primer

<400> SEQUENCE: 15
atcaggaccg gggtggaaac aattaccact ggc                              33

<210> SEQ ID NO 16
<211> LENGTH: 33
<212> TYPE: DNA
<213> ORGANISM: Artificial Sequence
<220> FEATURE:
<223> OTHER INFORMATION: Mutated Hepatitis C virus primer

<400> SEQUENCE: 16
gccagtggta attgtttcca ccccggtcct gat                              33
```